United States Patent
Gillette

(10) Patent No.: US 9,294,732 B2
(45) Date of Patent: Mar. 22, 2016

(54) SYSTEMS AND METHODS FOR SLEEP MONITORING

(71) Applicant: Good Sleep, LLC, Grand Blanc, MI (US)

(72) Inventor: Christopher J. Gillette, Battle Creek, MI (US)

(73) Assignee: Good Sleep LLC, Grand Blanc, MI (US)

( * ) Notice: Subject to any disclaimer, the term of this patent is extended or adjusted under 35 U.S.C. 154(b) by 490 days.

(21) Appl. No.: 13/778,317

(22) Filed: Feb. 27, 2013

(65) Prior Publication Data

US 2014/0049627 A1 Feb. 20, 2014

Related U.S. Application Data

(60) Provisional application No. 61/682,997, filed on Aug. 14, 2012.

(51) Int. Cl.
| | |
|---|---|
| *H04N 7/18* | (2006.01) |
| *A61B 5/00* | (2006.01) |
| *A61B 5/01* | (2006.01) |
| *A61B 5/0205* | (2006.01) |
| *A61B 5/03* | (2006.01) |

(Continued)

(52) U.S. Cl.
CPC ............... *H04N 7/18* (2013.01); *A61B 5/0002* (2013.01); *A61B 5/0006* (2013.01); *A61B 5/01* (2013.01); *A61B 5/02055* (2013.01); *A61B 5/03* (2013.01); *A61B 5/04012* (2013.01); *A61B 5/0432* (2013.01); *A61B 5/4806* (2013.01); *A61B 5/7225* (2013.01); *A61B 5/7475* (2013.01); *A61B 7/00* (2013.01); *A61B 5/0428* (2013.01); *A61B 5/0476* (2013.01); *A61B 5/0488* (2013.01); *A61B 5/0496* (2013.01); *A61B 5/11* (2013.01); *A61B 5/14542* (2013.01); *A61B 5/6843* (2013.01)

(58) Field of Classification Search
CPC ...... A61B 5/0002; A61B 5/0006; A61B 5/01; A61B 5/02055; A61B 5/03; A61B 5/04012; A61B 5/0428; A61B 5/0432; A61B 5/0476; A61B 5/0488; A61B 5/0496; A61B 5/11; A61B 5/14542; A61B 5/4806; A61B 5/06
See application file for complete search history.

(56) References Cited

U.S. PATENT DOCUMENTS

| | | | |
|---|---|---|---|
| 4,982,738 | A | 1/1991 | Griebel |
| 6,062,216 | A | 5/2000 | Corn |

(Continued)

*Primary Examiner* — Thai Tran
*Assistant Examiner* — Stephen Smith
(74) *Attorney, Agent, or Firm* — Harness, Dickey & Pierce, P.L.C.

(57) ABSTRACT

A mobile computing device for performing a sleep study includes a camera, a display, a processor, and a tangible computer readable medium. The tangible computer readable medium includes a sleep study application embodied as code for selectively displaying a request to capture an image of a user of the mobile computing device using the camera. The sleep study application further includes code for, after storage of the image: selectively prompting a data collection module to store data samples generated based on signals generated using at least one of an electromyography sensor connected to the user, an electroencephalography sensor connected to the user, an electrocardiogram sensor connected to the user, and an oxygen saturation sensor connected to the user, an electrooculography sensor connected to the user, a temperature sensor connected to the user, and a pressure sensor connected to the user; and receiving the data samples from the data collection module.

14 Claims, 11 Drawing Sheets

(51) Int. Cl.
*A61B 5/04* (2006.01)
*A61B 5/0432* (2006.01)
*A61B 7/00* (2006.01)
*A61B 5/0476* (2006.01)
*A61B 5/0488* (2006.01)
*A61B 5/0496* (2006.01)
*A61B 5/145* (2006.01)
*A61B 5/11* (2006.01)
*A61B 5/0428* (2006.01)

(56) References Cited

U.S. PATENT DOCUMENTS

| | | | |
|---|---|---|---|
| 6,454,724 B1 | 9/2002 | Greene | |
| 6,529,752 B2 | 3/2003 | Krausman et al. | |
| 7,508,307 B2 | 3/2009 | Albert | |
| 7,593,767 B1 | 9/2009 | Modarres | |
| 2002/0165462 A1 | 11/2002 | Westbrook et al. | |
| 2003/0026464 A1* | 2/2003 | Kamiyama | G01S 7/52098 382/128 |
| 2005/0102167 A1* | 5/2005 | Kapoor | A61B 5/0006 705/3 |
| 2007/0092112 A1* | 4/2007 | Awatsu | G06F 21/32 382/115 |
| 2007/0130287 A1* | 6/2007 | Kumar | A61N 1/08 709/217 |
| 2007/0208269 A1* | 9/2007 | Mumford | A61B 5/0002 600/546 |
| 2008/0076973 A1* | 3/2008 | Muradia | G06F 19/322 600/300 |
| 2008/0146277 A1* | 6/2008 | Anglin | G06F 19/3418 455/556.1 |
| 2008/0154111 A1 | 6/2008 | Wu et al. | |
| 2008/0214903 A1 | 9/2008 | Orbach | |
| 2008/0319277 A1 | 12/2008 | Bradley | |
| 2009/0054737 A1 | 2/2009 | Magar et al. | |
| 2009/0099471 A1 | 4/2009 | Broadley et al. | |
| 2009/0136094 A1* | 5/2009 | Driver | G06F 19/3406 382/115 |
| 2009/0157337 A1* | 6/2009 | Zhang | A61B 5/0402 702/65 |
| 2010/0017231 A1 | 1/2010 | Galbraith et al. | |
| 2010/0049006 A1 | 2/2010 | Magar et al. | |
| 2010/0063366 A1 | 3/2010 | Ochs et al. | |
| 2010/0100004 A1 | 4/2010 | van Someren | |
| 2010/0217100 A1 | 8/2010 | LeBoeuf et al. | |
| 2011/0004072 A1 | 1/2011 | Fletcher et al. | |
| 2011/0015495 A1* | 1/2011 | Dothie | A47C 31/123 600/300 |
| 2011/0190594 A1 | 8/2011 | Heit et al. | |
| 2011/0218409 A1 | 9/2011 | Kugler et al. | |
| 2011/0263950 A1* | 10/2011 | Larson | A61B 5/1113 600/301 |
| 2011/0267196 A1 | 11/2011 | Hu et al. | |
| 2011/0288379 A1 | 11/2011 | Wu | |
| 2011/0295083 A1 | 12/2011 | Doelling et al. | |
| 2011/0295102 A1 | 12/2011 | Lakkis et al. | |
| 2011/0305376 A1* | 12/2011 | Neff | G06F 19/327 382/128 |
| 2012/0053472 A1 | 3/2012 | Tran | |
| 2012/0088998 A1* | 4/2012 | Bardy | A61B 5/0006 600/382 |
| 2012/0185268 A1* | 7/2012 | Wiesner | G06Q 50/22 705/2 |
| 2012/0203078 A1* | 8/2012 | Sze | G06F 19/3418 600/301 |
| 2012/0313785 A1* | 12/2012 | Hanson | G08B 21/24 340/573.1 |
| 2013/0070153 A1* | 3/2013 | Hill | H04N 21/42228 348/569 |
| 2013/0144190 A1 | 6/2013 | Bruce et al. | |
| 2013/0218582 A1* | 8/2013 | LaLonde | A61B 5/686 705/2 |
| 2013/0245389 A1* | 9/2013 | Schultz | A61B 5/0002 600/301 |
| 2013/0317753 A1* | 11/2013 | Kamen | G06F 19/3412 702/19 |
| 2014/0114675 A1* | 4/2014 | Soon-Shiong | G06F 19/322 705/2 |
| 2014/0347392 A1* | 11/2014 | Odessky | A61B 5/1121 345/633 |
| 2014/0379369 A1* | 12/2014 | Kokovidis | G06F 19/3418 705/2 |
| 2015/0031964 A1* | 1/2015 | Bly | A61B 5/165 600/301 |

\* cited by examiner

SYSTEMS AND METHODS FOR SLEEP MONITORING

CROSS-REFERENCE TO RELATED APPLICATIONS

This application claims the benefit of U.S. Provisional Application No. 61/682,997, filed on Aug. 14, 2012. The entire disclosure of the application referenced above is incorporated herein by reference.

FIELD

The present disclosure relates to systems and methods for monitoring sleeping characteristics of a user.

BACKGROUND

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Sleep studies are tests involving recordation of various characteristics of a person while the person sleeps. A sleep study may be performed, for example, to help a health care professional (e.g., a doctor) diagnose whether a person has sleep apnea. A person having sleep apnea may stop breathing during sleep for at least a predetermined period, such as 10 seconds or more. Sleep studies may also be performed to aid a health care professional diagnose the presence of one or more other conditions.

Sleep studies are generally carried out at an accredited sleep center and are supervised by one or more qualified technologists. The carrying out of sleep studies at accredited sleep centers and under the supervision of one or more technologists may be done to ensure that data is properly measured and collected during the sleep studies.

SUMMARY

In a feature, a system for performing a sleep study is disclosed. A data collection module receives signals generated using at least one of an electromyography (EMG) sensor connected to a user, an electroencephalography (EEG) sensor connected to the user, an electrocardiogram (ECG) sensor connected to the user, and an oxygen saturation (SPO2) sensor connected to the user. A mobile computing device is implemented independently of the data collection module and communicates with the data collection module. The mobile computing device includes a processor and a tangible computer readable medium including a sleep study application embodied as code for: selectively prompting the data collection module to store data samples generated based on the signals; receiving the data samples from the data collection module; and transmitting sleep study data including the data samples to a first data server. The mobile computing device further includes a communications module that wirelessly downloads the sleep study application from a second data server.

In further features, the system further includes a data cable, and the data collection module and the mobile computing device communicate over the data cable.

In still further features, the data collection module and the mobile computing device communicate over the data cable in accordance with a Universal Serial Bus (USB) protocol.

In yet further features, the mobile computing device further includes a touchscreen display that displays data to the user and that receives input from the user.

In further features, the sleep study data further includes data input by the user to the mobile computing device.

In still further features, the data collection module receives signals generated using the EMG sensor, the EEG sensor, the ECG sensor, and the SPO2 sensor.

In yet further features, the system further includes: a movement sensor that measures movement of at least one of the user and the mobile computing device; and a microphone. The code is further for: selectively storing data samples generated based on signals from the movement sensor and the microphone; and transmitting the sleep study data further including the data samples generated based on signals from the movement sensor and the microphone.

In further features, the data collection module includes: a second tangible computer readable medium; an amplifier and filter module that filters and amplifies an ECG signal generated by the ECG sensor to produce a processed ECG signal; and an analog to digital converter module that selectively samples the processed ECG signal, that converts the samples into digital values to generate the data samples, and that stores the data samples in the second tangible computer readable medium.

In still further features, the data collection module includes: a second tangible computer readable medium; an amplifier and filter module that filters and amplifies an EEG signal generated by the EEG sensor to produce a processed EEG signal; and an analog to digital converter module that selectively samples the processed EEG signal, that converts the samples into digital values to generate the data samples, and that stores the data samples in the second tangible computer readable medium.

In yet further features, the system further includes: a sensor interface module that receives an SPO2 signal from the SPO2 sensor, that generates a processed SPO2 signal based on the SPO2 signal, and that outputs the processed SPO2 signal to the data collection module. The data collection module further includes: a second tangible computer readable medium; and a universal asynchronous receiver/transmitter (UART) module that receives the processed SPO2 signal and that stores data samples in the second tangible computer readable medium.

In another feature, a method for performing a sleep study is disclosed. The method includes: receiving, by a data collection module, signals generated using at least one of an electromyography (EMG) sensor connected to a user, an electroencephalography (EEG) sensor connected to the user, an electrocardiogram (ECG) sensor connected to the user, and an oxygen saturation (SPO2) sensor connected to the user; wirelessly downloading, by a mobile computing device, a sleep study application for performing the sleep study from a first data server; and executing, by the mobile computing device, the sleep study application including: selectively prompting the data collection module to store data samples generated based on the signals; receiving the data samples from the data collection module; and transmitting sleep study data including the data samples to a second data server. The mobile computing device is implemented independently of the data collection module.

In further features, the receiving the data samples from the data collection module includes receiving, by the mobile computing device, the data samples from the data collection module over a data cable.

In still further features, the method further includes transmitting, by the data collection module, the data samples over the data cable in accordance with a Universal Serial Bus (USB) protocol.

In yet further features, the method further includes: displaying, on a touchscreen display of the mobile computing device, data to the user; and receiving, from the touchscreen display, input from the user.

In further features, the transmitting sleep study data further includes transmitting data input by the user to the mobile computing device.

In still further features, the receiving signals generated using at least one of the EMG sensor, the EEG sensor, the ECG sensor, and the SPO2 sensor includes receiving, by the data collection module, signals generated using the EMG sensor, the EEG sensor, the ECG sensor, and the SPO2 sensor.

In yet further features, the method further includes: measuring, by a movement sensor, at least one of the user and the mobile computing device; and selectively storing, by the mobile computing device, data samples generated based on signals from the movement sensor and a microphone. The transmitting sleep study data further includes transmitting the data samples generated based on signals from the movement sensor and the microphone.

In further features, the method further includes: filtering and amplifying, by the data collection module, an ECG signal generated by the ECG sensor to produce a processed ECG signal; selectively sampling, by the data collection module, the processed ECG signal; converting, by the data collection module, the samples into digital values to generate the data samples; and storing, by the data collection module, the data samples in a second tangible computer readable medium of the data collection module.

In still further features, the method further includes: filtering and amplifying, by the data collection module, an EEG signal generated by the EEG sensor to produce a processed EEG signal; selectively sampling, by the data collection module, the processed EEG signal; converting, by the data collection module, the samples into digital values to generate the data samples; and storing, by the data collection module, the data samples in a second tangible computer readable medium of the data collection module.

In yet further features, the method further includes: receiving, by a sensor interface module, an SPO2 signal from the SPO2 sensor; generating, by the sensor interface module, a processed SPO2 signal based on the SPO2 signal; outputting, by the sensor interface module, the processed SPO2 signal to the data collection module; receiving, by the data collection module, the processed SPO2 signal; and storing, by the data collection module, data samples in a second tangible computer readable medium of the data collection module.

In another feature, a data collection module for performing a sleep study is described. The data collection module includes: a first module that receives an electrocardiogram (ECG) signal from an ECG sensor connected to a user; a second module that receives an electroencephalography (EEG) signal from an EEG sensor connected to the user; and a collection control module. The collection control module: communicates with a mobile computing device; in response to a prompt from the mobile computing device, stores data samples generated based on the ECG and EEG signals in a tangible computer readable medium; and selectively transmits the data samples to the mobile computing device.

In further features, the collection control module communicates with the mobile computing device over a data cable connected at a first end to the data collection module and at a second end to the mobile computing device.

In still further features, in response to the prompt, the collection control module further stores data samples generated based on an electromyography (EMG) signal from an EMG sensor in the tangible computer readable medium.

In yet further features, in response to the prompt, the collection control module further stores data samples generated based on an oxygen saturation (SPO2) signal from an SPO2 sensor in the tangible computer readable medium.

In still further features: the first module amplifies and filters the ECG signal to produce a processed ECG signal; and, in response to the prompt from the mobile computing device, the collection control module stores data samples generated based on the processed ECG signal in the tangible computer readable medium.

In further features, the collection control module samples the processed ECG signal at a predetermined rate, digitizes the samples to produce digital values, and stores the digital values in the tangible computer readable medium.

In yet further features, the first module filters the ECG signal using a high pass filter (HPF) and a low pass filter (LPF).

In still further features: the second module amplifies and filters the EEG signal to produce a processed EEG signal; and, in response to the prompt from the mobile computing device, the collection control module stores data samples generated based on the processed EEG signal in the tangible computer readable medium.

In further features, the collection control module samples the processed EEG signal at a predetermined rate, digitizes the samples to produce digital values, and stores the digital values in the tangible computer readable medium.

In still further features, the collection control module transmits the data samples to the mobile computing device in response to a determination that a predetermined number of data samples have been stored.

In yet another feature, a method includes: receiving, by a data collection module, an electrocardiogram (ECG) signal from an ECG sensor connected to a user; receiving, by the data collection module, an electroencephalography (EEG) signal from an EEG sensor connected to the user; communicating, by the data collection module, with a mobile computing device; in response to a prompt from the mobile computing device, storing, by the data collection module, data samples generated based on the ECG and EEG signals in a tangible computer readable medium; and selectively transmitting, by the data collection module, the data samples to the mobile computing device.

In further features, the communicating includes communicating, by the data collection module, with the mobile computing device over a data cable connected at a first end to the data collection module and at a second end to the mobile computing device.

In still further features, the method further includes storing, by the data collection module in response to the prompt, data samples generated based on an electromyography (EMG) signal from an EMG sensor in the tangible computer readable medium.

In further features, the method further includes storing, by the data collection module in response to the prompt, data samples generated based on an oxygen saturation (SPO2) signal from an SPO2 sensor in the tangible computer readable medium.

In yet further features, the method further includes: amplifying and filtering the ECG signal, by the data collection module, to produce a processed ECG signal; and storing, by the data collection module in response to the prompt, data samples generated based on the processed ECG signal in the tangible computer readable medium.

In yet further features, the method further includes: sampling, by the data collection module, the processed ECG signal at a predetermined rate; digitizing, by the data collection module, the samples to produce digital values; and storing, by the data collection module, the digital values in the tangible computer readable medium.

In further features, the filtering comprises filtering the ECG signal using a high pass filter (HPF) and a low pass filter (LPF).

In yet further features, the method further includes: amplifying and filtering the EEG signal, by the data collection module, to produce a processed EEG signal; and storing, by the data collection module in response to the prompt, data samples generated based on the processed EEG signal in the tangible computer readable medium.

In still further features, the method further includes: sampling, by the data collection module, the processed EEG signal at a predetermined rate; digitizing, by the data collection module, the samples to produce digital values; and storing, by the data collection module, the digital values in the tangible computer readable medium.

In further features, the method further includes transmitting, by the data collection module, the data samples to the mobile computing device in response to a determination that a predetermined number of data samples have been stored.

In yet another feature, a mobile computing device for performing a sleep study is described. The mobile computing device includes: a processor; a tangible computer readable medium including a sleep study application embodied as code. The code is for: selectively prompting a data collection module to store data samples generated based on signals generated using at least one of an electromyography (EMG) sensor connected to a user, an electroencephalography (EEG) sensor connected to the user, an electrocardiogram (ECG) sensor connected to the user, and an oxygen saturation (SPO2) sensor connected to the user; receiving the data samples from the data collection module; and transmitting sleep study data including the data samples to a first data server. The mobile computing device further includes a communications module that wirelessly downloads the sleep study application from a second data server.

In further features, the code is for prompting the data collection module to store the data samples in response to at least one user input.

In still further features, the mobile computing device further includes a touchscreen display that displays data to the user and that receives input from the user.

In yet further features, the code is further for verifying proper connection of leads the at least one of the ECG, EEG, EMG, and SPO2 sensors to the user.

In further features, the sleep study data further includes data input by the user to the mobile computing device.

In still further features, a system includes: the mobile computing device; and a movement sensor that measures movement of at least one of the user and the mobile computing device. The code is further for: selectively storing data samples generated based on signals from the movement sensor; and transmitting the sleep study data further including the data samples generated based on signals from the movement sensor.

In further features, a system includes: the mobile computing device; and a microphone. The code is further for: selectively storing data samples generated based on signals from the microphone; and transmitting the sleep study data further including the data samples generated based on signals from the microphone.

In still further features, the code is further for: selectively displaying a health insurance portability and accountability act (HIPAA) waiver; and selectively prompting the data collection module to begin collecting the data samples in response to receipt of predetermined user input indicative of acceptance of the HIPAA waiver.

In yet further features, the code is further for: selectively displaying terms of a release for data samples collected during the sleep study; and selectively prompting the data collection module to begin collecting the data samples in response to receipt of predetermined user input indicative of acceptance of the terms of the release.

In further features, the code is further for selectively prompting the data collection module to begin collecting the data samples in response to receipt of a digital signature of the user.

In another feature, a method includes: selectively prompting, by a mobile computing device, a data collection module to store data samples generated based on signals generated using at least one of an electromyography (EMG) sensor connected to a user, an electroencephalography (EEG) sensor connected to the user, an electrocardiogram (ECG) sensor connected to the user, and an oxygen saturation (SPO2) sensor connected to the user; receiving, by the mobile computing device, the data samples from the data collection module; transmitting, by the mobile computing device, sleep study data including the data samples to a first data server; and wirelessly downloading, by the mobile computing device, the sleep study application from a second data server.

In further features, the selectively prompting includes prompting, by the mobile computing device, the data collection module to store the data samples in response to at least one user input.

In still further features, the method further includes: displaying, by the mobile computing device, data to the user on a touchscreen display; and receiving, by the mobile computing device, input from the user from the touchscreen display.

In yet further features, the method further includes verifying, by the mobile computing device, proper connection of leads the at least one of the ECG, EEG, EMG, and SPO2 sensors to the user.

In further features, the method further includes transmitting, by the mobile computing device, the sleep, study data further including data input by the user to the mobile computing device.

In still further features, the method further includes: selectively storing, by the mobile computing device, data samples generated based on signals from a movement sensor; and transmitting, by the mobile computing device, the sleep study data further including the data samples generated based on signals from the movement sensor.

In yet further features, the method further includes: selectively storing, by the mobile computing device, data samples generated based on signals from a microphone; and transmitting, by the mobile computing device, the sleep study data further including the data samples generated based on signals from the microphone.

In further features, the method further includes: selectively displaying, by the mobile computing device, a health insurance portability and accountability act (HIPAA) waiver; and selectively prompting, by the mobile computing device, the data collection module to begin collecting the data samples in response to receipt of predetermined user input indicative of acceptance of the HIPAA waiver.

In still further features, the method further includes: selectively displaying, by the mobile computing device, terms of a release for data samples collected during the sleep study; and selectively prompting, by the mobile computing device, the data collection module to begin collecting the data samples in response to receipt of predetermined user input indicative of acceptance of the terms of the release.

In yet further features, the method further includes selectively prompting, by the mobile computing device, the data collection module to begin collecting the data samples in response to receipt of a digital signature of the user.

In yet another feature, a mobile computing device for performing a sleep study is described. The mobile computing device includes a camera, a display, a processor, and a tangible computer readable medium. The tangible computer readable medium includes a sleep study application embodied as code for: selectively displaying a request to capture an image of a user of the mobile computing device using the camera; and storing the image. The sleep study application further includes code for, after the storage of the image: selectively prompting a data collection module to store data samples generated based on signals generated using at least one of an electromyography (EMG) sensor connected to the user, an electroencephalography (EEG) sensor connected to the user, an electrocardiogram (ECG) sensor connected to the user, and an oxygen saturation (SPO2) sensor connected to the user, an electrooculography (EOG) sensor connected to the user, a temperature sensor connected to the user, and a pressure sensor connected to the user; and receiving the data samples from the data collection module.

In further features, the sleep study application further includes code for displaying the request to capture an image of the user in response to a determination that the at least one of the EMG sensor, the EEG sensor, the ECG sensor, the SPO2 sensor, the EOG sensor, the temperature sensor, and the pressure sensor is/are properly connected to the user.

In yet further features, the sleep study application further includes code for prompting the data collection module to stop storing data samples generated based on the signals in response to disconnection of at least one of the EMG sensor, the EEG sensor, the ECG sensor, the SPO2 sensor, the EOG sensor, the temperature sensor, and the pressure sensor.

In still further features, the sleep study application further includes code for, in response to a determination that the at least one of the EMG sensor, the EEG sensor, the ECG sensor, the SPO2 sensor, the EOG sensor, the temperature sensor, and the pressure sensor have/has been re-connected, displaying a second request to capture a second image of the user.

In further features, the sleep study application further includes code for selectively prompting the data collection module to continue storing data samples generated based on the signals after storage of the second image.

In yet further features, the sleep study application further includes code for prompting the data collection module to stop storing data samples generated based on the signals in response to disconnection of the EMG sensor, the ECG sensor, and the EOG sensor.

In still further features, the sleep study application further includes code for prompting the data collection module to stop storing data samples generated based on the signals in response to disconnection of the SPO2 sensor.

In further features, the sleep study application further includes code for prompting the data collection module to store data samples generated based on the signals in response to the storage of the image.

In yet further features, the sleep study application further includes code for transmitting sleep study data including the data samples and the image to a data server.

In still further features, the sleep study application further includes code for displaying video obtained using the camera while displaying the request to capture an image of the user.

In yet another feature, a method for performing a sleep study is described. The method includes: selectively displaying on a display, by a mobile computing device, a request to capture an image of a user of the mobile computing device using a camera of the mobile computing device; and storing, by the mobile computing device, the image in a tangible computer readable medium. The method further includes, after the storage of the image: selectively prompting, by the mobile computing device, a data collection module to store data samples generated based on signals generated using at least one of an electromyography (EMG) sensor connected to the user, an electroencephalography (EEG) sensor connected to the user, an electrocardiogram (ECG) sensor connected to the user, and an oxygen saturation (SPO2) sensor connected to the user, an electrooculography (EOG) sensor connected to the user, a temperature sensor connected to the user, and a pressure sensor connected to the user; and receiving, by the mobile computing device, the data samples from the data collection module.

In further features, the method further includes displaying, by the mobile computing device, the request to capture an image of the user in response to a determination that the at least one of the EMG sensor, the EEG sensor, the ECG sensor, the SPO2 sensor, the EOG sensor, the temperature sensor, and the pressure sensor is/are properly connected to the user.

In yet further features, the method further includes prompting, by the mobile computing device, the data collection module to stop storing data samples generated based on the signals in response to disconnection of at least one of the EMG sensor, the EEG sensor, the ECG sensor, the SPO2 sensor, the EOG sensor, the temperature sensor, and the pressure sensor.

In still further features, the method further includes, in response to a determination that the at least one of the EMG sensor, the EEG sensor, the ECG sensor, the SPO2 sensor, the EOG sensor, the temperature sensor, and the pressure sensor have/has been re-connected, displaying, by the mobile computing device, a second request to capture a second image of the user.

In further features, the method further includes selectively prompting, by the mobile computing device, the data collection module to continue storing data samples generated based on the signals after storage of the second image.

In yet further features, the method further includes prompting, by the mobile computing device, the data collection module to stop storing data samples generated based on the signals in response to disconnection of the EMG sensor, the ECG sensor, and the EOG sensor.

In still further features, the method further includes prompting, by the mobile computing device, the data collection module to stop storing data samples generated based on the signals in response to disconnection of the SPO2 sensor.

In further features, the method further includes prompting, by the mobile computing device, the data collection module to store data samples generated based on the signals in response to the storage of the image.

In yet further features, the method further includes transmitting, by the mobile computing device, sleep study data including the data samples and the image to a data server.

In still further features, the method further includes displaying on the display, by the mobile computing device, video obtained using the camera while displaying the request to capture an image of the user.

Further areas of applicability of the present disclosure will become apparent from the detailed description, the claims and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein.

In the drawings, reference numbers may be reused to identify similar and/or identical elements.

DETAILED DESCRIPTION

There is a need for systems and methods for patients to accurately and completely perform a sleep study outside of an accredited sleep center and without the supervision of one or more qualified technologists, such as at home. Such systems and methods provide various benefits including, but not limited to: eliminating the need for a patient to travel to a sleep center; eliminating a patient's apprehension associated with conducting a sleep study at a sleep center; and decreasing the time necessary to complete a sleep study by eliminating the need to schedule the sleep study in the future with a sleep center.

Figure 1:
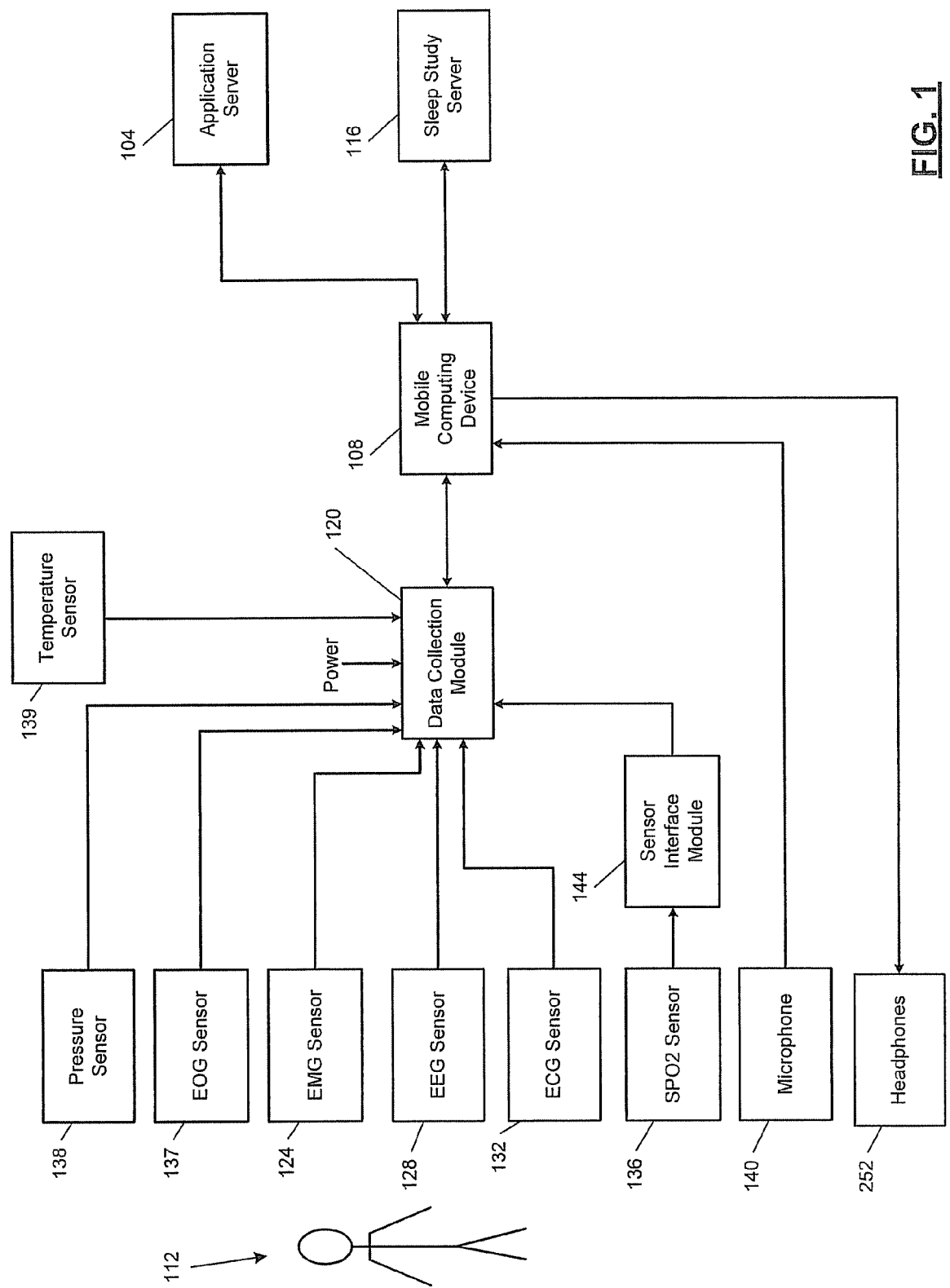
FIG. 1 is a functional block diagram of an example sleep study system.

Referring now to FIG. 1, a functional block diagram of an example sleep study system is presented. An application server 104 stores one or more applications including a sleep study application. The sleep study application can be executed by mobile computing devices, such as mobile computing device 108, to perform a sleep study. The sleep study application is embodied as code stored on a computer-readable medium.

Mobile computing devices can wirelessly download the sleep study application from the application server 104. For example, the mobile computing device 108 can download the sleep study application from the application server 104 in response to input from a patient 112. The mobile computing device 108 may include, for example, a cellular phone, a tablet computer, a portable media player, or another suitable type of portable computing device.

A prescriber (e.g., a doctor) can prescribe a sleep study for the patient 112 via a sleep study server 116. Using one or more unique identifiers associated with the patient 112, the patient 112 can perform the sleep study at any location, such as at home. The patient 112 performs the sleep study using the mobile computing device 108, the sleep study application, a data collection module 120, and one or more user devices, such as an electromyography (EMG) sensor 124, an electroencephalography (EEG) sensor 128, an electrocardiogram (ECG) sensor 132, an oxygen saturation (SPO2) sensor 136, a microphone 140, an electrooculography (EOG) sensor 137, a pressure sensor 138, and a temperature sensor 139.

The EMG sensor 124 generates signals based on electrical activity of one or more muscles of the body of the patient 112. The EEG sensor 128 generates signals based on electrical activity of the brain of the patient 112. The ECG sensor 132 generates signals based on electrical activity of the heart of the patient 112. The SPO2 sensor 136 generates signals based on oxygen saturation of blood of the patient 112. The EOG sensor 137 generates signals based on eye movement of the patient 112. The pressure sensor 137 generates signals based on pressures in one or more airways of the patient 112. The temperature sensor 139 generates signals based on one or more temperatures of the patient 112.

The data collection module 120 may receive power from an external power source, such as a standard wall outlet. Additionally or alternatively, the data collection module 120 may include an energy storage device, which may or may not be rechargeable, such as one or more batteries.

The data collection module 120 receives signals from the EMG sensor 124, the EEG sensor 128, the ECG sensor 132, the EOG sensor 137, the pressure sensor 138, and the temperature sensor 139. The data collection module 120 receives signals from the SPO2 sensor 136 via a sensor interface module 144. The sensor interface module 144 processes the signals generated by the SPO2 sensor 136 and provides processed SPO2 signals to the data collection module 120.

Figure 2:
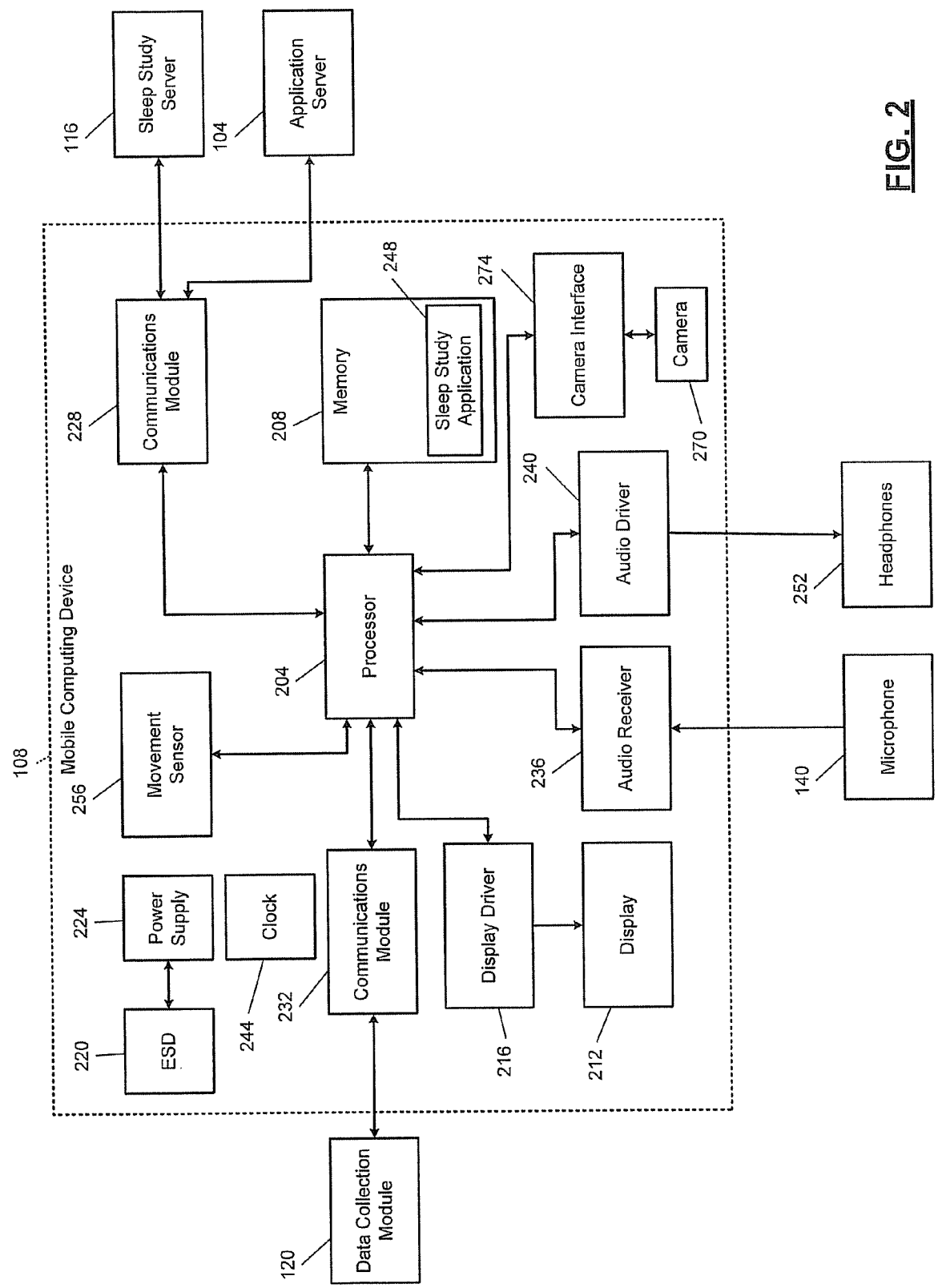
FIG. 2 is a functional block diagram of an example implementation of a mobile computing device.

FIG. 2 is a functional block diagram of an example implementation of the mobile computing device 108. Referring now to FIGS. 1 and 2, the mobile computing device 108 may include a processor 204, memory 208, a touch display 212, a display driver 216, an energy storage device (ESD) 220, and a power supply 224. The mobile computing device 108 may also include a first communications module 228, a second communications module 232, an audio receiver 236, an audio driver 240, and a clock 244.

The energy storage device 220 may include one or more re-chargeable batteries. The power supply 224 may provide power to various components of the mobile computing device 108 based on power from the energy storage device 220 and/or an external power supply, such as a standard wall outlet. The touch display 212 may include any touch-sensitive display device, such as a capacitive sensing display. The touch display 212 may display information to the patient 112 and receive input from the patient 112. The processor 204 controls the display driver 216 to control what is displayed on the touch display 212.

For example only, a physical character layout (e.g., a partial or whole QWERTY-based keyboard) may displayed on a portion of the touch display 212 as needed as a "soft keyboard", and the patient 112 may input information to the mobile computing device 108 via the touch display 212 using one or more fingers. Different portions or functions of a partial or whole standard QWERTY keyboard may also be selectively displayed via the touch display 212. The patient 112 may additionally or alternatively input information to the mobile computing device 108 via the touch display 212 using a stylus, a mouse, a trackball, or the like.

While the display is discussed as being a touch display, a non-touch screen display may be used in conjunction with one or more user input devices, such as a partial or whole QWERTY-based keyboard (not shown). The patient 112 may additionally or alternatively interface the mobile computing device 108 via one or more other user input devices, such as buttons, switches, etc.

The first communications module 228 communicates with the application server 104 wirelessly via one or more antennas (not shown). The first communications module 228 or another communications module communicates with the sleep study server 116 wirelessly via one or more antennas (also not shown). Once downloaded from the application server 104, the sleep study application is stored in the memory 208 or another suitable tangible computer-readable medium, as illustrated by 248.

The second communications module 232 communicates with the data collection module 120 using a cable. For example, the data collection module 120 and the mobile computing device 108 may communicate via a universal serial bus (USB) protocol or another suitable wired network communication protocol. While communication between the data collection module 120 and the mobile computing device 108 is discussed as being performed by wire, the data collection module 120 and the mobile computing device 108 may communicate wirelessly.

The audio receiver 236 receives signals from the microphone 140. The audio receiver 236 may also receive signals from one or more microphones of the mobile computing device 108, which are not shown. The audio receiver 236 processes the signals from the microphone(s) for use with a sleep study performed using the sleep study application (e.g., to identify snoring).

The processor 204 controls the audio driver 240 to control audio output of one or more audio output devices, such as headphones 252 and/or one or more speakers of the mobile computing device 108. For example, the audio output device(s) may be used to provide "white noise" to facilitate sleeping during a sleep study. In various implementations, the headphones 252 and the microphone 140 are integrated into a combined unit that includes both the headphones 252 and the microphone 140. The clock 244 tracks a current date time.

The mobile computing device 108 may also include one or more movement sensors, such as movement sensor 256. For example only, movement sensors may include one or more accelerometers, a global positioning system (GPS), and/or one or more other sensors based upon which movement of the mobile computing device 108 and/or the patient 112 can be detected. Movement of the mobile computing device 108 and/or the patient 112 can be used with a sleep study performed using the sleep study application. While movement sensors that are internal to the mobile computing device 108 are shown, the movement sensor(s) may instead be implemented within the data collection module 120 or independently.

The mobile computing device 108 includes one or more cameras, such as camera 270. For example only, the mobile computing device 108 may include one or more cameras implemented on the same surface of the mobile computing device 108 as the display 212. The mobile computing device 108 may also include one or more cameras implemented on a surface of the mobile computing device 108 opposite to that of the display 212.

The processor 204 may receive data from the camera 270 via a camera interface 274. The processor 204 may, for example, selectively display real-time video from the camera 270 on the display 212 and selectively display images acquired using the camera 270 on the display 212. The processor 204 may also control operation of the camera 270 via the camera interface 274.

Figure 3A:
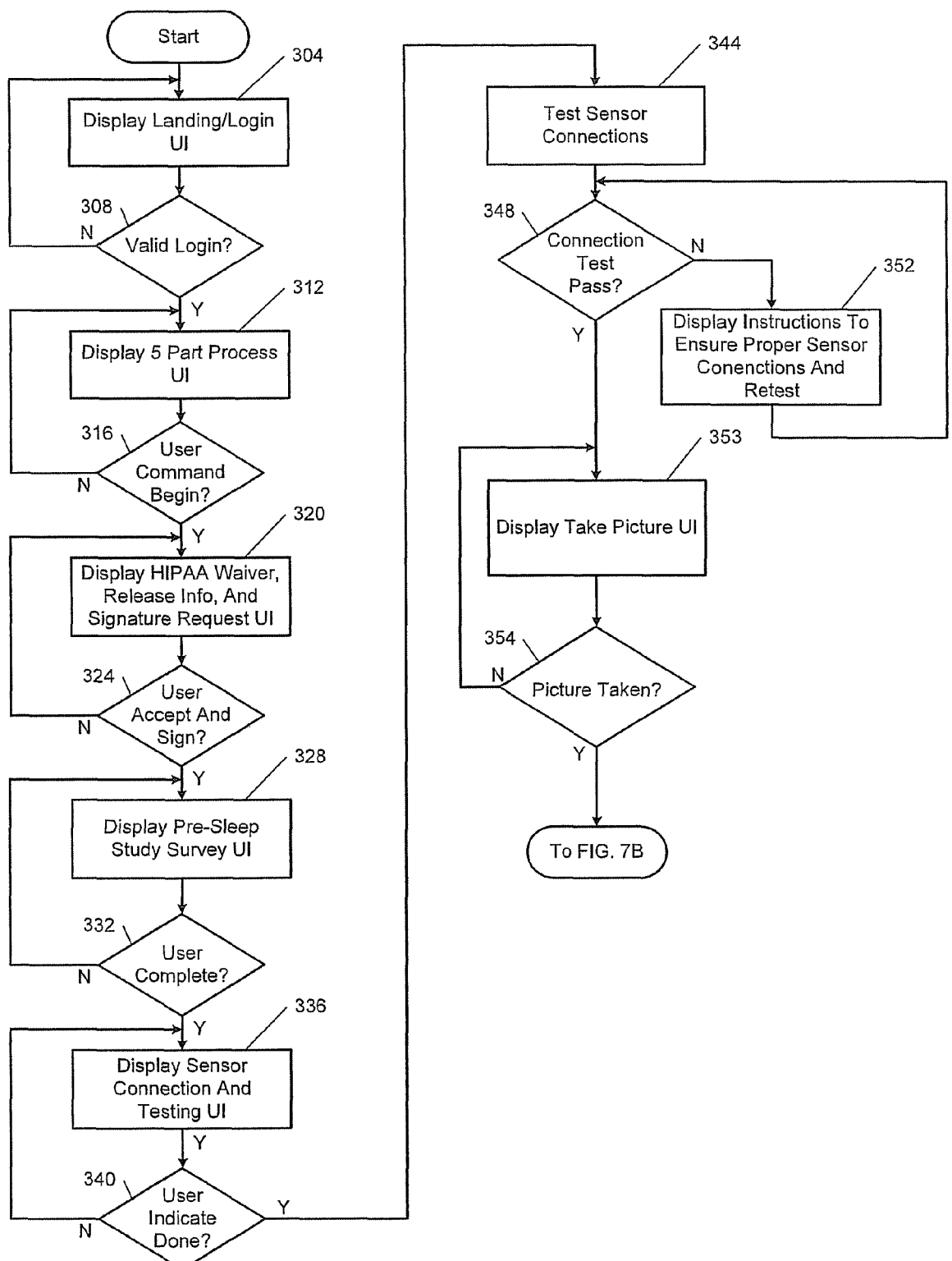
FIGS. 3A-B include a flowchart depicting an example method of conducting a sleep study that may be performed by a mobile computing device executing a sleep study application.
Figure 3B:
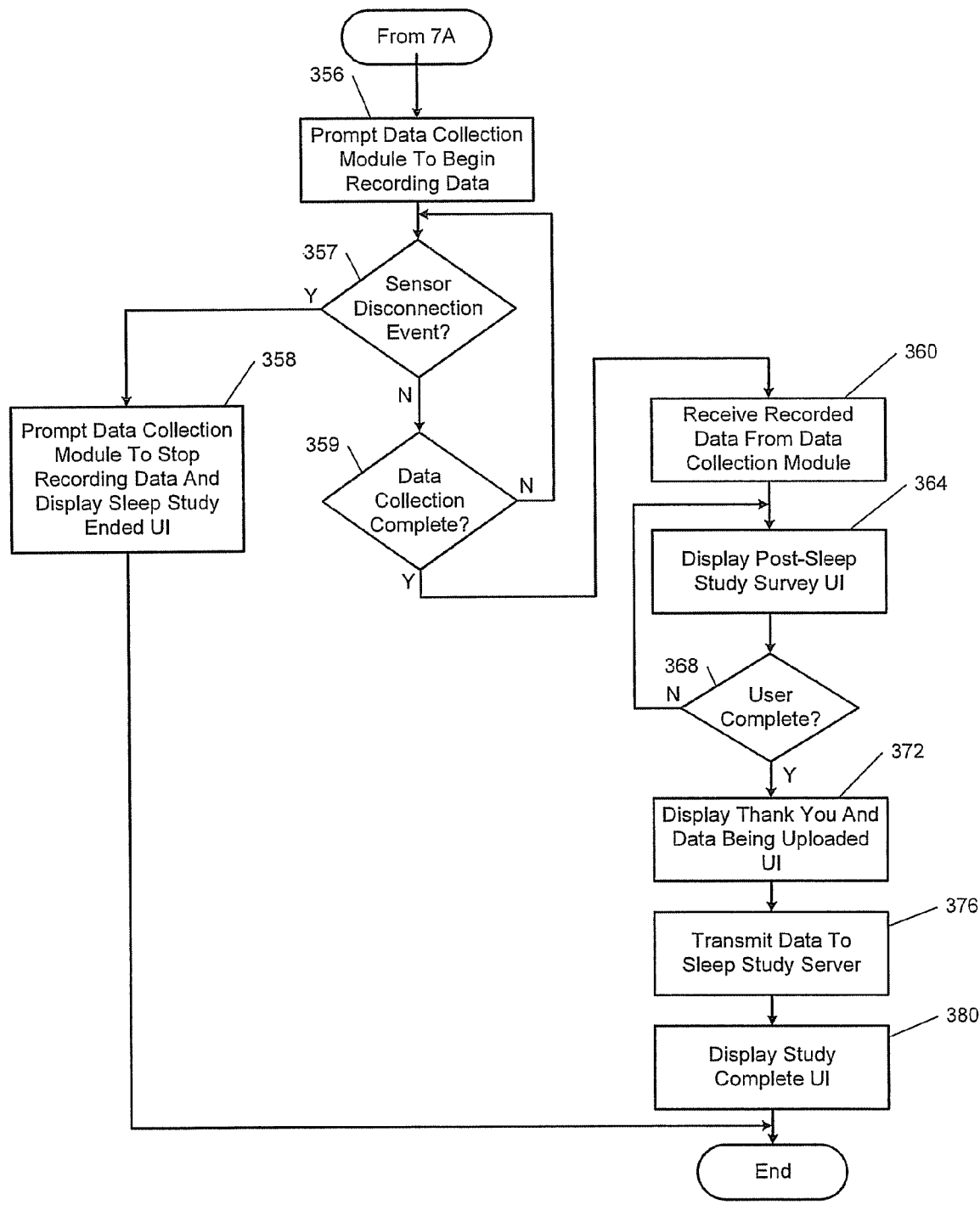

FIGS. 3A-3B include a flowchart depicting an example method of conducting a sleep study that may be performed by the mobile computing device 108 executing the sleep study application. Referring now to FIGS. 1-3B, control may begin in response to the patient 112 triggering execution of the sleep study application via the mobile computing device 108.

At 304, the mobile computing device 108 displays a landing and login user interface (UI) on the touch display 212. The landing and login UI may include one or more fields for the patient 112 to input one or more unique identifiers of the patient 112, such as a username and password. The username and password may be, for example, provided to the patient 112 or set by the patient 112 in response to the prescription of the sleep study by the prescriber. While the example of a username and password are discussed, other unique identifiers of the patient 112 may be used in various implementations. The unique identifier(s) of the patient 112 may be used to authenticate the patient 112.

At 308, it is determined whether the input provided by the patient 112 is valid. For example, the mobile computing device 108 may transmit the input to the sleep study server 116 and the sleep study server 116 may perform the determination, or the determination may be performed by the mobile computing device 108. If 308 is true, control continues with 312. If 308 is false, control may return to 304 to continue displaying the landing and login UI on the touch display 212.

The mobile computing device 108 displays a five part process UI on the touch display 212 at 312. The five part process UI indicates individual parts of the sleep study. For example, five parts of the sleep study may include: (1) an agreement and signature portion; (2) a pre-sleep study survey portion; (3) a sensor connection and testing portion; (4) a data collection portion; and (5) a post-sleep study survey and data transfer portion. Each of the portions are discussed further below. The five part process UI may also include an indicator of one or more predetermined actions to be taken by the patient 112 to begin the sleep study.

At 316, the mobile computing device 108 determines whether the patient 112 has performed the predetermined action(s) to begin the sleep study. If 316 is true, control continues with 320. If 316 is false, control may remain at 312 to continue displaying the five part process UI.

The mobile computing device 108 displays an agreement UI on the touch display 212 at 320. The agreement UI includes an indicator of one or more predetermined actions to be taken by the patient 112 to accept the terms and conditions of a health insurance portability and accounting act (HIPAA) waiver. The agreement indicator also includes an indicator of one or more predetermined actions to be taken by the patient 112 to view the HIPAA waiver. The mobile computing device 108 displays the HIPAA waiver on the touch display 212 in response to the patient performing the predetermined action(s) to view the HIPAA waiver.

The agreement UI also includes an indicator of one or more predetermined actions to be taken by the patient 112 to accept the terms and conditions of a data release form for release of data collected during the sleep study. The agreement UI also includes an indicator of one or more predetermined actions to be taken by the patient 112 to view the data release form. The mobile computing device 108 displays the data release form on the touch display 212 in response to the patient performing the predetermined action(s) to view the data release form.

The agreement UI also includes a field for the patient 112 to input a digital signature, such as using a finger or a stylus. The agreement UI also includes an indicator of one or more predetermined actions to be taken by the patient 112 to continue with the sleep study. At 324, it is determined whether the patient 112 performed the predetermined action(s) to accept the terms and conditions of the HIPAA waiver, performed the predetermined action(s) to accept the terms and conditions of the data release form, input a digital signature, and performed the predetermined action(s) to continue with the sleep study. If 324 is true, control continues with 328. If 324 is false, control may remain at 320 to continue displaying the agreement UI. The determination may be performed by the mobile computing device 108 or by the sleep study server 116.

At 328, the mobile computing device 108 displays a pre-sleep study survey UI on the touch display 212. The pre-sleep study survey UI includes one or more predetermined questions for the patient 112 and indicators for inputting answers to the predetermined questions. The pre-sleep study survey UI also includes an indicator of one or more predetermined actions to be taken by the patient 112 to continue with the sleep study.

At 332, it is determined whether the patient 112 input answers for each of the predetermined questions and performed the predetermined action(s) to continue with the sleep study. If 332 is true, control continues with 336. If 332 is false, control may remain at 328, and the mobile computing device 108 may continue displaying the pre-sleep study survey UI. The determination may be performed by the mobile computing device 108 or by the sleep study server 116.

The mobile computing device 108 displays a sensor connection and testing UI. The sensor connection and testing UI may include indicators of how to connect the EMG sensor 124, the EEG sensor 128, the ECG sensor 132, the EOG sensor 137, the pressure sensor 138, the temperature sensor 139, and the SPO2 sensor 136 to the body of the patient 112. The sensor connection and testing UI may also include an indicator of one or more predetermined actions to be taken by the patient 112 to begin checking for proper connection of the sensors 124-139 to the body of the patient 112.

At 340, the mobile computing device 108 may determine whether the patient 112 has performed the predetermined action(s) to begin checking for proper connection of the sensors 124-139 to the body of the patient 112. If 340 is true, control may continue with 344. If 340 is false, control may remain at 336, and the mobile computing device 108 may continue displaying the sensor connection and testing UI. The determination may be performed by the mobile computing device 108 or by the sleep study server 116.

The mobile computing device 108 tests whether the sensors 124-139 are properly connected to the body of the patient 112 at 344. For example, the mobile computing device 108 may attempt to receive one or more samples of data from each of the sensors 124-139 at 344. The mobile computing device 108 receives samples of data from the sensors 124-139 from the data collection module 120.

At 348, the mobile computing device 108 determines whether the connection of the sensors 124-139 to the body of the patient 112 is correct. If 348 is false, the mobile computing device 108 may display instructions for properly connecting one or more of the sensors 124-139 that are not properly connected on the touch display 212 and re-test the connections at 352, and control may return to 348. If 348 is true, the mobile computing device 108 may display that the sensors 124-139 are properly connected on the touch display 212, and control may continue with 353.

The mobile computing device 108 may display a take a picture UI on the touch display 212 at 353. The take a picture UI may instruct the patient 112 to take a picture of the patient 112 while wearing the (properly connected) sensors. The mobile computing device 108 may also initialize the camera 270 to ready the camera 270 for picture taking at 353. The mobile computing device 108 may also display real-time video obtained via the camera 270 on the touch display 212 at 353. The mobile computing device 108 may also display one or more features on the touch display 212 for centering the patient 112 within a viewing area of the camera 270 at 353.

At 354, the mobile computing device 108 may determine whether a picture of the patient 112 has been obtained. If 354 is true, control may continue with 356 of FIG. 7B. If 354 is false, control may return to 353 and continue displaying the take a picture UI on the touch display 212. The mobile computing device 108 may store a picture taken by the patient 112. The picture may help verify that the data collected during the sleep study was actually data for the patient 112 as opposed to another person.

Referring now to FIG. 3B, the mobile computing device 108 prompts the data collection module 120 to begin collecting data samples from the sensors 124-139 at 356. For example, the mobile computing device 108 may transmit a signal to begin collecting data samples to the data collection module 120 over the cable or wirelessly. The mobile computing device 108 may also begin collecting data from the movement sensor 256 and the microphone 140 at 356. Data from the movement sensor 256 and the microphone 140 may be used in conjunction with data from the sensors 124-139. The mobile computing device 108 may stamp data from the movement sensor 256 and the microphone 140 with a date and time tracked by the clock 244.

At 357, the mobile computing device 108 may determine a sensor disconnection event has occurred. A sensor disconnection event may occur when one or more sensors have been disconnected from the patient 112. Sensor disconnection events are discussed further below in conjunction with the examples of FIGS. 10A-B. If 357 is true, at 358 the mobile computing device 108 may prompt the data collection module 120 to stop collecting data samples and display a sleep study ended UI. The sleep study ended UI indicates that the sleep study was ended before the sleep study was completed and to begin a sleep study again. If 357 is false, control may continue with 359.

At 359, the mobile computing device 108 may determine whether data collection for the sleep study is complete. Data may be collected until one or more predetermined data collection ending conditions occur. For example only, the predetermined data collection ending conditions may include, but are not limited to, passing of a predetermined period (e.g., 6 hours), collection of a predetermined number of data samples, the patient 112 taking one or more predetermined actions via the mobile computing device 108, and/or one or more other suitable conditions. The data collection module 120 stores data samples from the sensors 124-139 within the data collection module 120 until the one or more predetermined data collection ending conditions occur. If 359 is false, control may return to 357. If 359 is true, control may continue with 360.

At 360, once the one or more predetermined data collection ending conditions occur, the mobile computing device 360 receives (from the data collection module 120) the data samples collected by the data collection module 120. The mobile computing device 360 stores the data samples received from the data collection module 120 in the memory 208.

At 364, the mobile computing device 108 displays a post-sleep study survey UI on the touch display 212. The post-sleep study survey UI includes one or more predetermined questions for the patient 112 and indicators for inputting answers to the predetermined questions. The pre-sleep study survey UI also includes an indicator of one or more predetermined actions to be taken by the patient 112 to continue towards completion of the sleep study.

At 368, it is determined whether the patient 112 input answers for each of the predetermined questions and performed the predetermined action(s) to continue towards completion of the sleep study. If 368 is true, control continues with 372. If 368 is false, control may remain at 364, and the mobile computing device 108 may continue displaying the post-sleep study survey UI. The determination may be performed by the mobile computing device 108 or by the sleep study server 116.

The mobile computing device 108 displays a thank you and data transferring UI on the touch display 212 at 372. The thank you and data transferring UI thanks the patient 112 for performing the sleep study using the sleep study application. The thank you and data transferring UI also includes an indicator that the mobile computing device 108 is transferring data collected for and during the sleep study to the sleep study server 116 and an indicator to refrain from disabling the communicating abilities of the mobile computing device 108.

At 376, the mobile computing device 108 communicates the data collected for and during the sleep study to the sleep study server 116. The communicated data includes the acceptance of the HIPAA waiver and the information release form, the digital signature of the patient 112, the answers to the pre-sleep study survey, the answers to the post-sleep study survey, the data samples collected from the sensors 124-139, and data collected from the movement sensor 256 and the microphone 140. The communicated data may also include the picture taken by the patient 112. The communicated data may also include other data pertaining to the performance of the sleep study, such as location, ambient conditions, data regarding the connection of the sensors 124-139, etc. The mobile computing device 108 may display a sleep study complete UI at 380. The sleep study complete UI may indicate that performance of the sleep study and the transfer of collected data to the sleep study server 116 is complete.

Once the sleep study is complete, the mobile computing device 108 may selectively display data collected during the sleep study on the touch display 212. For example, the mobile computing device 108 may generate and display one or more traces of collected data versus time on the touch display 212.

Figure 4:
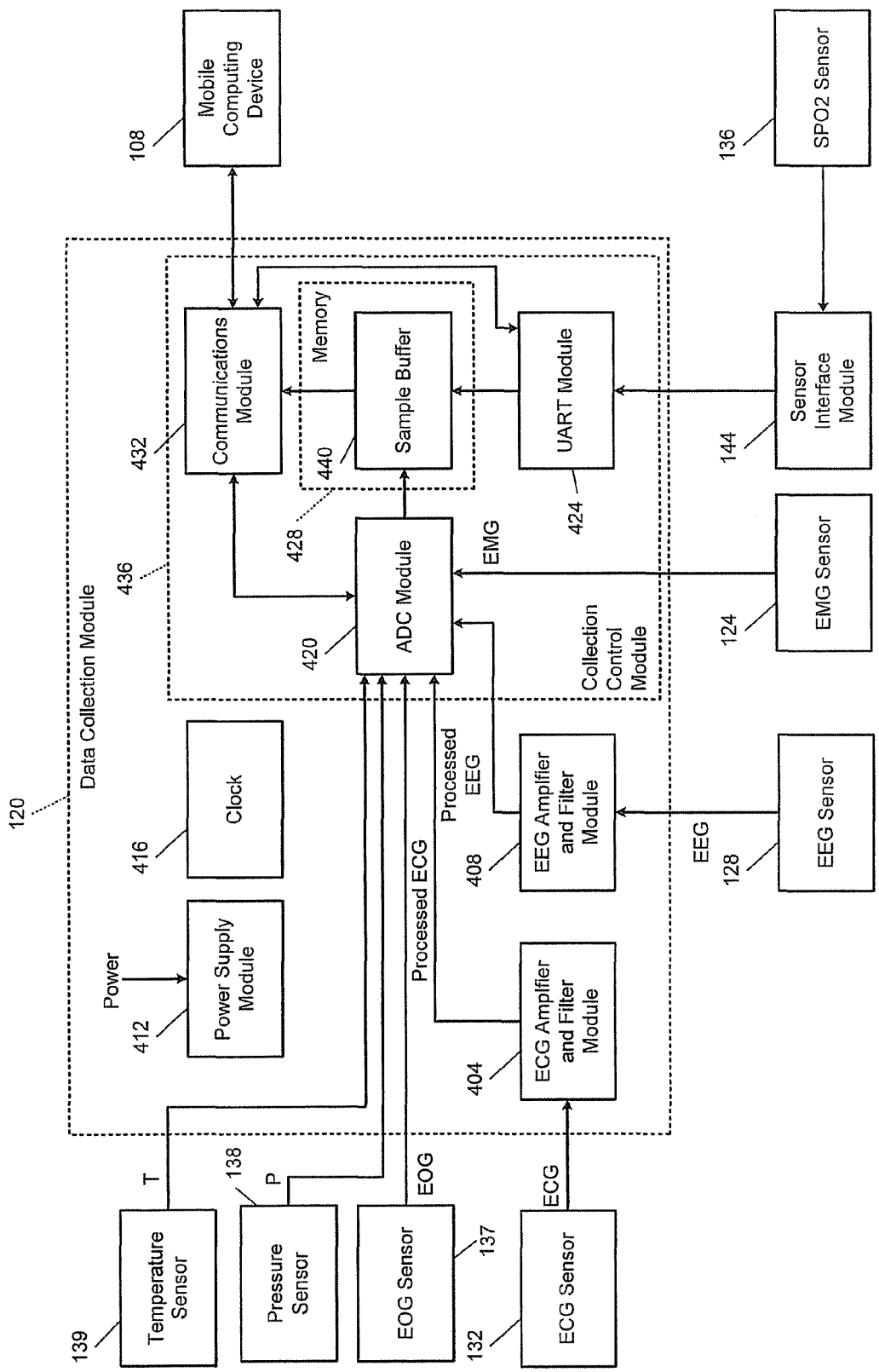
FIG. 4 is a functional block diagram of an example implementation of a data collection module.

Referring now to FIG. 4, a functional block diagram of an example implementation of the data collection module 120 is presented. The data collection module 120 may include an ECG amplifier and filter module 404, an EEG amplifier and filter module 408, a power supply module 412, and a clock 416. The data collection module 120 may also include an analog to digital converter (ADC) module 420, a universal asynchronous receiver/transmitter (UART) module 424, memory 428, and a communications module 432. In various implementations, the ADC module 420, the UART module 424, the memory 428, and the communications module 432 may be implemented within a collection control module 436, such as a PIC24-based microcontroller (e.g., PIC24FJ64GB02) or another suitable type of controller.

The power supply 412 provides power to various components of the data collection module 120, such as the ADC module 420, the UART module 424, the communications module 432, the memory 428, the ECG amplifier and filter module 404, the EEG amplifier and filter module 408, and the clock 416. The power supply 412 may output power based on power received from one or more energy storage devices, such as one or more batteries, and/or an external power supply, such as a standard wall outlet. The clock 416 tracks a current time and date.

Figure 5:
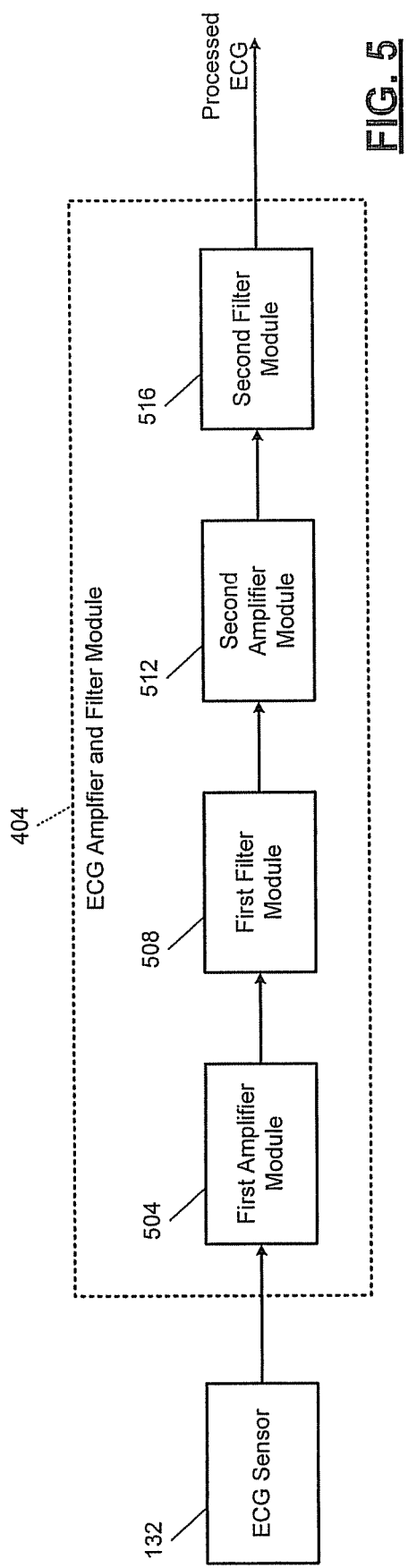
FIG. 5 is a functional block diagram of an example implementation of an electrocardiogram (ECG) amplifier and filter module.

The ECG amplifier and filter module 404 receives the signals generated by the ECG sensor 132. The ECG amplifier and filter module 404 performs one or more signal processing functions on the signals generated by the ECG sensor 132 and generates a processed ECG signal. FIG. 5 includes a functional block diagram of an example implementation of the ECG amplifier and filter module 404.

Referring now to FIGS. 4 and 5, the ECG amplifier and filter module 404 may include a first amplifier module 504, a first filter module 508, a second amplifier module 512, and a second filter module 516. The first amplifier module 504 may provide an amplifier gain of approximately 50 or another suitable value. The first filter module 508 may include a high pass filter (HPF) and have a cutoff frequency ($f_0$) of approximately 0.03 Hertz or another suitable value. The second amplifier module 512 may provide an amplifier gain of approximately 10 or another suitable value. The second filter module 516 may include a low pass filter (LPF).

Figure 6:
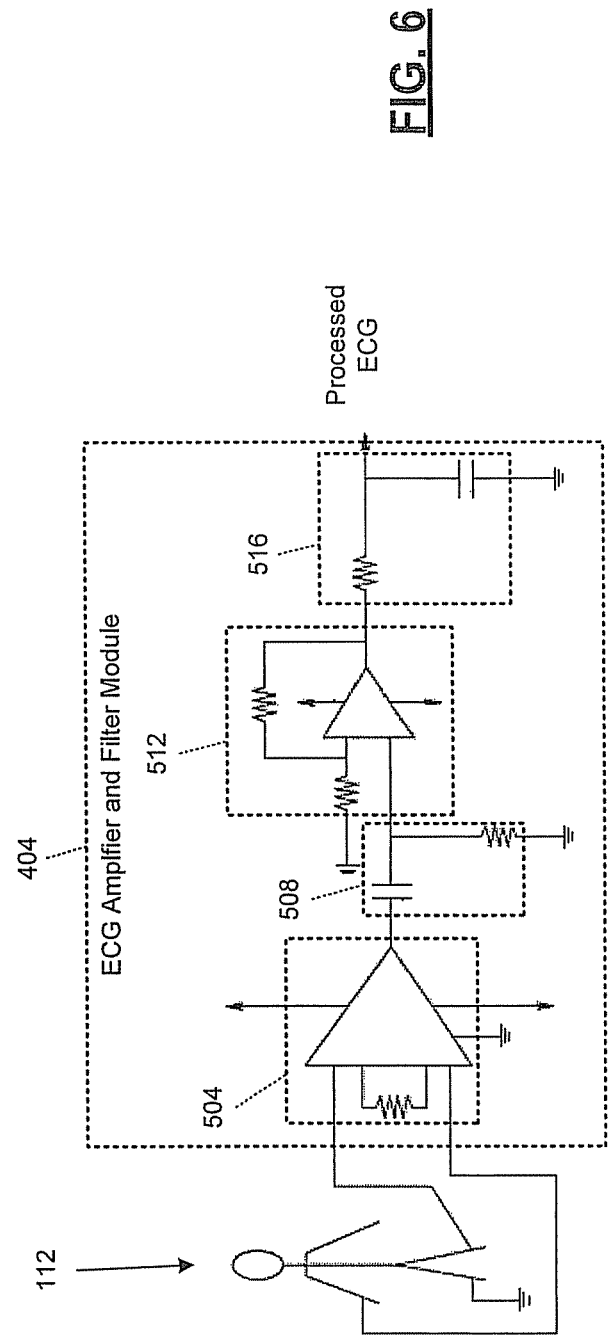
FIG. 6 is an example schematic of the ECG amplifier and filter module.

FIG. 6 includes an example schematic of the ECG amplifier and filter module 404. Referring now to FIGS. 4-6, the ECG sensor 132 may include three electrical connectors (leads) for connection with the skin of the patient 112. For example, as shown in FIG. 6, a first electrical connector may be connected to a first location on the skin of the patient 112 (e.g., hand or arm), a second electrical connector may be connected to a second location on the skin of the patient 112 (e.g., a leg or foot), and a third electrical connector may be connected to a third location on the skin of the patient 112 (e.g., another leg or foot). While the example of three electrical connectors is shown and discussed, the ECG sensor 132 may include another suitable number of electrical connectors.

The third electrical connector may be connected to a ground (reference) potential. The first amplifier module 504 may include a first differential amplifier. The first and second electrical connectors may be connected to negative and positive inputs of the first differential amplifier. A resistor, such as a 1 kilo-Ohm resistor, may be connected between two terminals of the first differential amplifier. Positive and negative values of a reference potential (e.g., +/−6 Volts) may be connected at two terminals of the first differential amplifier. Another terminal of the first differential amplifier may be connected to the ground potential. The first differential amplifier generates a first output based on the signals received at the positive and negative inputs.

The first filter module 508 may include a first capacitor and a first resistor. The first capacitor may receive the first output (from the first differential amplifier) at a first terminal and be connected at a second terminal to an output node. A first terminal of the first resistor is also connected to the output node, and a second terminal of the first resistor may be connected to the ground potential. The first capacitor and the first resistor filter the first output to generate a second output at the output node. For example only, the first capacitor may include a 1000 micro-Farad capacitor, and the first resistor may include a 5.6 kilo-Ohm resistor.

The second amplifier module 512 may include a second differential amplifier, a second resistor, and a third resistor. A positive input of the second differential amplifier may be connected to the output node (of the first filter module 508). A negative input of second differential amplifier may be connected to a first node. The second resistor may be connected at a first end to the first node and at a second end to the ground potential. The third resistor may be connected at a first end to the first node and at a second end to an output terminal of the second differential amplifier. The positive and negative values of the reference may be connected at two terminals of the second differential amplifier. For example only, the first and second resistors may include 1 kilo-Ohm resistors. The second differential amplifier generates a second output based on the signals received at its positive and negative inputs.

The second filter module 516 may include a fourth resistor and a second capacitor. The fourth resistor may receive the second output (from the second differential amplifier) at a first terminal and be connected at a second terminal to a second output node. A first terminal of the second capacitor is also connected to the second output node, and a second terminal of the second capacitor may be connected to the ground potential. The fourth resistor and the second capacitor filter the second output to generate the processed ECG signal at the second output node.

Figure 7:
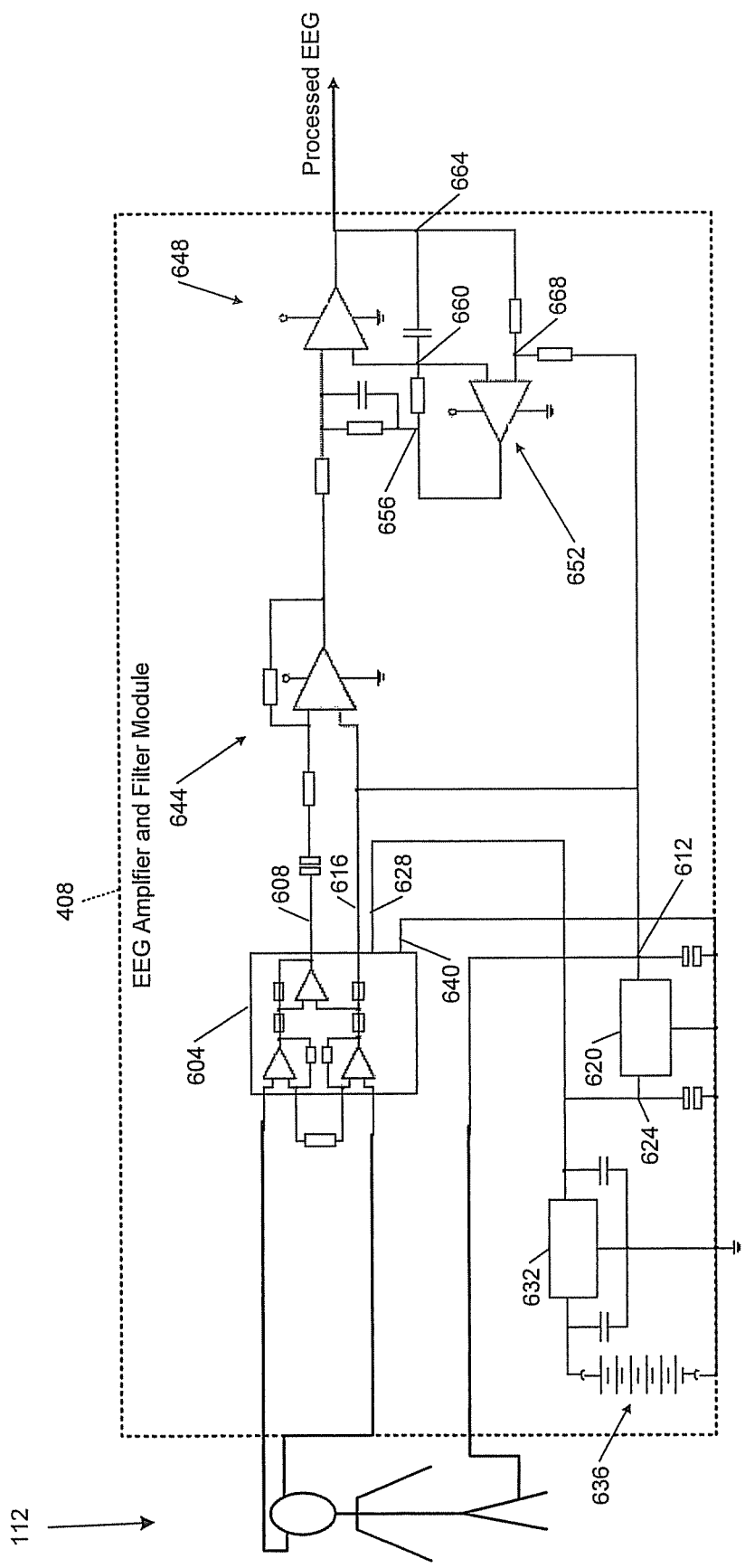
FIG. 7 is a functional block diagram and schematic of an example implementation of an electroencephalography (EEG) amplifier and filter module.

Referring again to FIG. 4, the EEG amplifier and filter module 408 receives the signals generated by the EEG sensor 128. The EEG amplifier and filter module 408 performs one or more signal processing functions on the signals generated by the EEG sensor 128 and generates a processed EEG signal. FIG. 7 includes a functional block diagram and schematic of an example implementation of the EEG amplifier and filter module 408. The EEG amplifier and filter module 408 may amplify the (relatively small in magnitude) signals generated by the EEG sensor 128 and filter artifacts from the signals (e.g., artifacts associated with blinking and eye movements) to generate the processed EEG signal.

Figure 8:
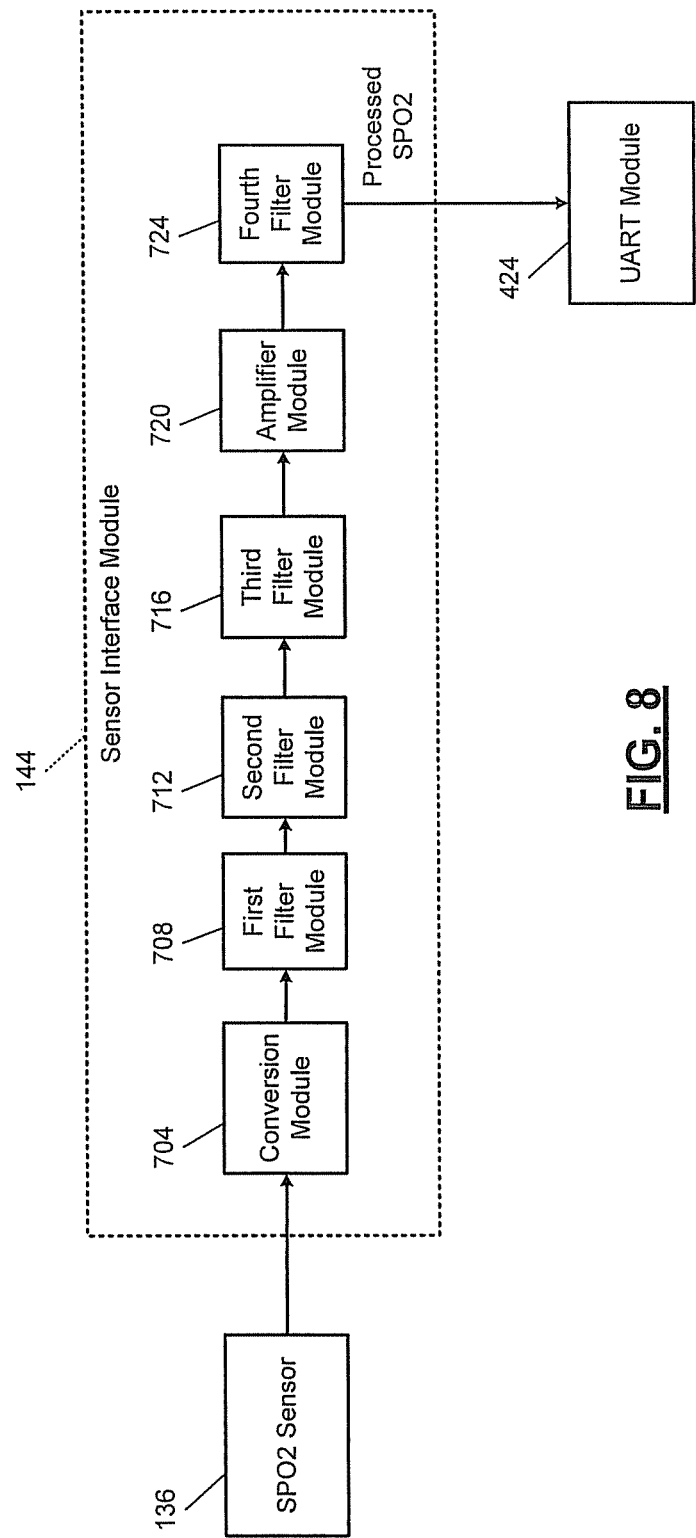
FIG. 8 is a functional block diagram of an example implementation of a sensor interface module.

Referring now to FIGS. 4 and 8, the EEG sensor 128 may include three electrical connectors (leads) for connection with the skin of the patient 112. For example, a fourth electrical connector may be connected to a fourth location on the skin of the patient 112 (e.g., one side of the head), a fifth electrical connector may be connected to a fifth location on the skin of the patient 112 (e.g., other side of the head) and a sixth electrical connector may be connected to the third location on the skin of the patient 112 (e.g., the right leg). While the example of three electrical connectors is shown and discussed, the EEG sensor 128 may include another suitable number of electrical connectors.

The fourth and fifth electrical connectors (of the EEG sensor 128) may be connected to first and second input terminals of a third amplifier module 604. For example only, the third amplifier module 604 may include an INA118P amplifier or another suitable type of amplifier. A gain resistor may be connected between third and fourth terminals of the third amplifier module 604. The third amplifier module 604 may generate a third output at a fifth terminal 608 based on the signals received at the first and second input terminals.

The sixth connector (of the EEG sensor 128) may be connected to a virtual ground node 612. A sixth terminal of the third amplifier module 604 is also connected to the virtual ground node 612. An output terminal of a virtual ground module 620, such as a TLE2426 virtual ground circuit, is also connected to the virtual ground node 612.

An input terminal of the virtual ground module 620 is connected to a positive reference potential node 624. A seventh terminal 628 of the third amplifier module 604 is also connected to the positive reference potential node 624. An output terminal of a voltage regulator module 632, such as a 7805T voltage regulator circuit, is connected to the positive reference potential node 624.

An input terminal of the voltage regulator module 632 is connected to a positive reference potential of a power source 636, such as a 9 Volt battery or another suitable power source. A negative reference potential of the power source 636 is connected to a ground reference potential. The voltage regulator module 632 adjusts power received from the power source 636 to produce a target reference potential at the positive reference potential node 624.

An eighth terminal 640 of the third amplifier module 604 is connected to the ground reference potential. First and second capacitors and are connected between the virtual ground node 612 and the ground reference potential and between the positive reference potential node 624 and the ground reference potential, respectively. Third and fourth capacitors and are connected between the input terminal of the voltage regulator module 632 and the ground reference potential and between the output terminal of the voltage regulator module 632 and the ground reference potential, respectively. For example only, the first and second capacitors may be 10 micro-Farad capacitors, the third capacitor may be a 0.33 micro-Farad capacitor, and the fourth capacitor may be a 0.1 micro-Farad capacitor.

A fifth capacitor and a resistor are connected between the fifth terminal 608 of the third amplifier module 604 and a positive input terminal of a second amplifier module 644. A negative input terminal of the sixth amplifier module 644 may be connected to the virtual ground node 612. For example only, the fifth capacitor may be a 10 micro-Farad capacitor, the resistor may be a 1 kilo-Ohm resistor, and the sixth amplifier module 644 may be a TLC272P amplifier circuit. A second resistor is connected between the positive input terminal of the sixth amplifier module 644 and an output terminal of the sixth amplifier module 644. For example only, the second resistor may be a 47 kilo-Ohm resistor. Fourth and fifth terminals of the sixth amplifier module 644 may be connected to the positive reference potential node 624 and the ground reference potential, respectively.

A third resistor may be connected between the output terminal of the sixth amplifier module 644 and a positive input terminal of a seventh amplifier module 648. A fourth resistor and a sixth capacitor may be connected between the input terminal of the seventh amplifier module 648 and an output terminal of an eighth amplifier module 652. For example only, the third resistor may be a 47 kilo-Ohm resistor, the fourth resistor may be a 33 kilo-Ohm resistor, the sixth capacitor may be a 0.1 micro-Farad capacitor, and the seventh and eighth amplifiers 648 and 652 may be TLC272P amplifier circuits.

A fifth resistor may be connected between a node 656 connecting the fourth resistor and the sixth capacitor to the output terminal of the eighth amplifier module 652 and a node 660 connecting a negative input terminal of the seventh amplifier module 648 with a negative input terminal of the eighth amplifier module 652. A seventh capacitor may be connected between the node 660 and a node 664 connected to an output terminal of the seventh amplifier module 648. For example only, the fifth resistor may be a 47 kilo-Ohm resistor, and the seventh capacitor may be a 0.1 micro-Farad capacitor.

The EEG amplifier and filter module 408 outputs the processed EEG signal via the output terminal of the seventh amplifier module 648. A sixth resistor may be connected between the node 664 and a node 668 connected to a positive input terminal of the eighth amplifier module 652. A seventh resistor may be connected between the node 668 and the virtual ground node 612. For example only, the sixth and seventh resistors may be 100 kilo-Ohm resistors. Fourth and fifth terminals of the seventh and eighth amplifiers 648 and 652 may be connected to the positive reference potential node 624 and the ground reference potential, respectively. The resistors and capacitors provide a filter, such as low pass filter with a cutoff frequency of approximately 33.86 Hertz, for the signals input to the seventh amplifier module 648.

Referring back to FIG. 4, the ECG amplifier and filter module 404 outputs the processed ECG signal to the ADC module 420. The EEG amplifier and filter module 408 also outputs the processed EEG signal to the ADC module 420. The signals generated by the EMG sensor 124 may be directly input to the ADC module 420. While the signals generated by the EMG sensor 124 are shown and described as being directly input to the ADC module 420, the signals generated by the EMG sensor 124 may be processed and/or filtered before being input to the ADC module 420.

The signals generated by the EOG sensor 137 may be directly input to the ADC module 420. While the signals generated by the EOG sensor 137 are shown and described as being directly input to the ADC module 420, the signals generated by the EOG sensor 137 may be processed and/or filtered before being input to the ADC module 420.

The signals generated by the pressure sensor 138 may be directly input to the ADC module 420. While the signals generated by the pressure sensor 138 are shown and described as being directly input to the ADC module 420, the signals generated by the pressure sensor 138 may be processed and/or filtered before being input to the ADC module 420.

The signals generated by the temperature sensor 139 may be directly input to the ADC module 420. While the signals generated by the temperature sensor 139 are shown and described as being directly input to the ADC module 420, the signals generated by the temperature sensor 139 may be processed and/or filtered before being input to the ADC module 420.

The sensor interface module 144 receives the signals generated by the SPO2 sensor 136. The SPO2 sensor 136 may be a disposable (one-time use) SPO2 sensor or a non-disposable (multiple-time use) SPO2 sensor. The sensor interface module 144 performs one or more signal processing functions on the signals generated by the SPO2 sensor 136 and generates a processed SPO2 signal. For example only, the sensor interface module 144 may include an OEM III Module or an Xpod by Nonin. The sensor interface module 144 outputs instantaneous values. In various implementations, the sensor interface module 144 may also output average values. In various implementations, the sensor interface module 144 and the SPO2 sensor 136 may be integrated within one device.

FIG. 8 includes a functional block diagram of an example implementation of the sensor interface module 144. Referring now to FIG. 8, the sensor interface module 144 may include a conversion module 704, a first filter module 708, a second filter module 712, a third filter module 716, an amplifier module 720, and a fourth filter module 724.

The conversion module 704 receives signals (current) from the SPO2 sensor 136 and converts the signals into voltage signals. The first filter module 708 filters the voltage signals to produce a first filtered signal. For example only, the first filter module 708 may include a low pass filter (LPF) with a cutoff frequency of approximately 6 Hertz. The first filter module 708 filters the first filtered signal to produce a second filtered signal. For example only, the second filter module 712 may include a 60 Hertz notch filter.

Figure 9:
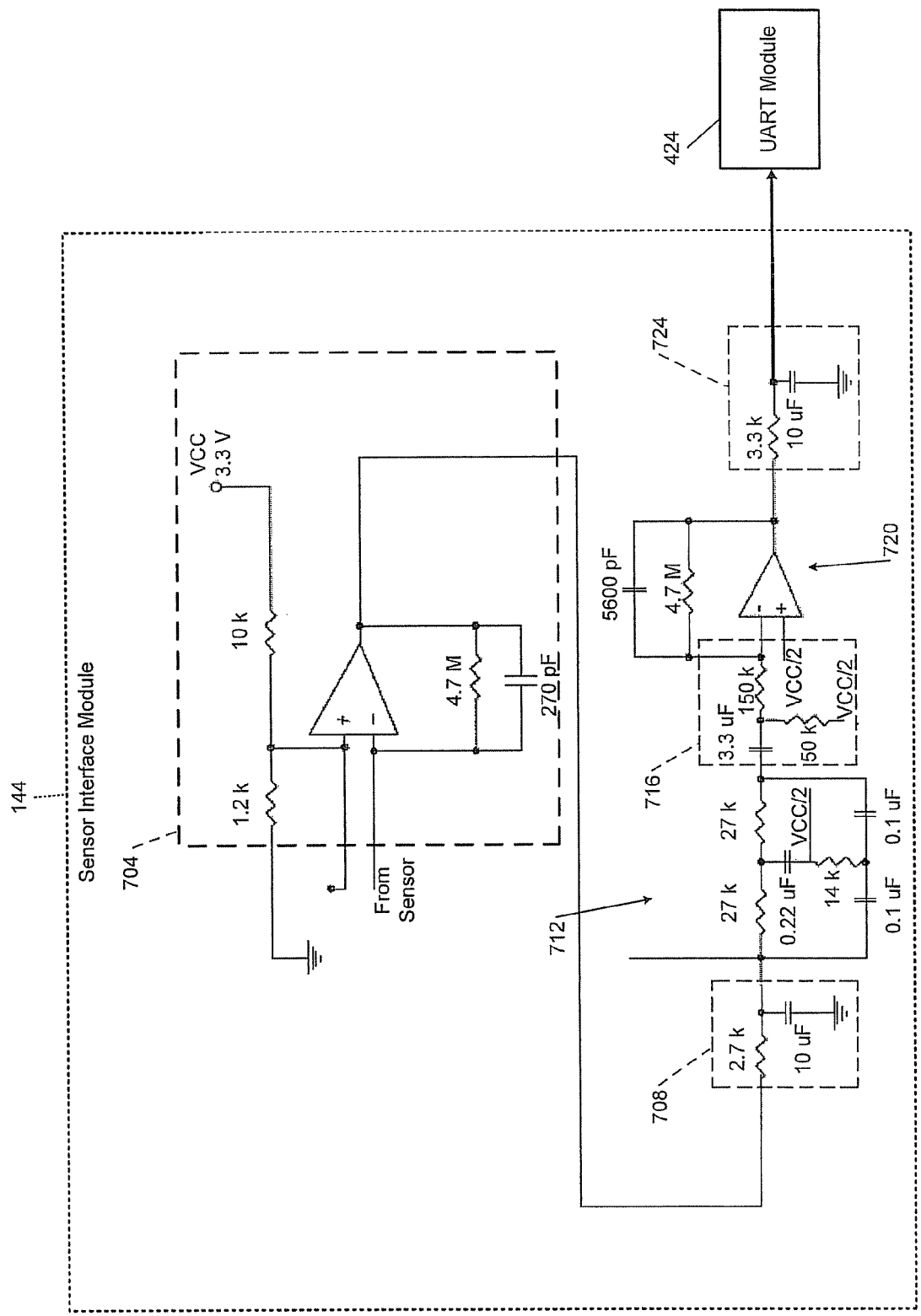
FIG. 9 is an example schematic of the sensor interface module.

The third filter module 716 filters the second filtered signal to produce a third filtered signal. For example only, the third filter module 716 may include a high pass filter (HPF) with a cutoff frequency of approximately 0.8 Hertz. The amplifier module 720 amplifiers the third filtered signal to produce an amplified signal. For example only, the amplifier module 720 may provide an amplifier gain of approximately 31 or another suitable gain. The fourth filter module 724 filters the amplified signal to produce the processed SPO2 signal and outputs the processed SPO2 signal to the UART module 424. For example only, the fourth filter module 724 may include a LPF with a cutoff frequency of approximately 4.8 Hz. FIG. 9 includes a schematic of an example implementation of the sensor interface module 144.

Referring back to FIG. 4, the EOG sensor 137 may include a plurality of electrical connectors (leads) for connection with the skin of the patient 112. For example, an electrical connector may be connected to the fourth location on the skin of the patient 112 (e.g., one side of the head), another electrical connector may be connected to the fifth location on the skin of the patient 112 (e.g., other side of the head), and another electrical connector may be connected to the third location on the skin of the patient 112 (e.g., the right leg). While the example of three electrical connectors is shown and discussed, the EOG sensor 137 may include another suitable number of electrical connectors.

The pressure sensor 138 may include one or more pressure transducers that measure pressure within a nasal cannula inserted into nostrils of the patient 112. The temperature sensor 139 may include one or more thermocouples that measure temperature within the nostrils of the patient 112 and temperature of air near a mouth of the patient 112.

In response to being triggered, the ADC module 420 samples the (analog) signals and converts the samples into corresponding digital values. The ADC module 420 stores the digital values in a sample buffer 440. The ADC module 420 may sample the signals at the same rate or at one or more different rates. For example, the ADC module 420 may generate digital values based on the processed ECG and EEG signals at a first predetermined rate (e.g., once every 2 milliseconds) and generate digital values based on the EMG signal at a second predetermined rate (e.g., once every 4 milliseconds). Digital values may be stored with timestamps or in the order in which they are generated.

In response to being triggered, the UART module 424 selectively stores digital values generated based on the signals from the SPO2 sensor 136 in the sample buffer 440. The communications module 432 triggers the ADC module 420 and the UART module 424 in response receipt of a signal from the mobile computing device 108 prompting the data collection module 120 to begin collecting data samples from the sensors 124-139.

The communications module 432 may reset a sample counter value to a predetermined reset value, such as zero, when triggering the ADC module 420 and the UART module 424. The communications module 432 may increment the sample counter value each time that one or more digital values are stored in the sample buffer 440. The communications module 432 may determine whether the sleep study is complete based on the sample counter value. For example, the communications module 432 may determine that the sleep study is complete when the sample counter value is greater than a predetermined value and determine that the sleep study is not yet complete when the sample counter is less than the predetermined value. The communications module 432 may alternatively determine that the sleep study is complete in response to receipt of a signal from the mobile computing device 108 indicating that the sleep study is complete. While the functions of resetting of the sample counter value, incrementing the sample counter, and determining whether the sleep study is complete are discussed as being performed by the communications module 432, one or more of the functions may be performed by the ADC module 420 and/or the UART module 424. When the sleep study is complete, the communications module 432 transmits data stored in the sample buffer 440 to the mobile computing device 108, and the mobile computing device 108 can later transmit data collected to the sleep study server 116.

Figure 10A:
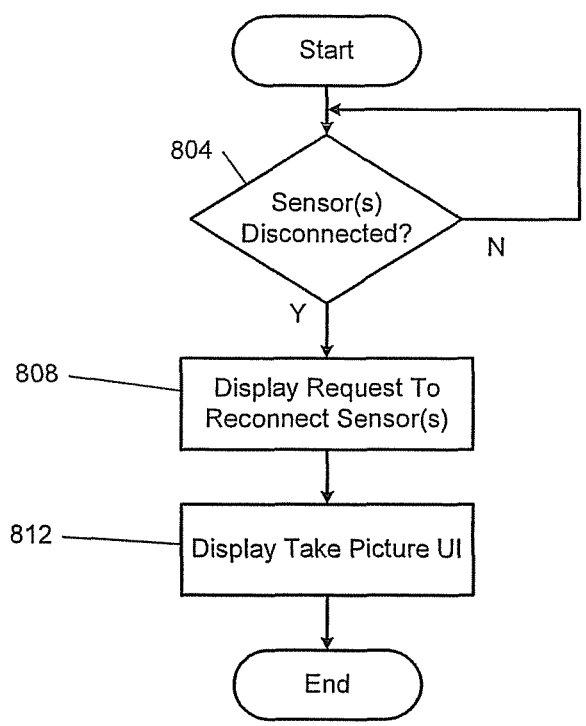
FIGS. 10A and 10B are flowcharts depicting example methods of collecting data during a sleep study.

FIG. 10A is a flowchart depicting an example method of collecting data during a sleep study that may be performed by the mobile computing device 108 executing the sleep study application is presented. Referring now to FIG. 10A, control may begin while the data collection module 120 is collecting data samples for the sleep study.

At 804, the mobile computing device 108 may determine whether one or more of the sensors 124-139 have been disconnected from the patient 112. If 804 is false, control may remain at 804, and the data collection module 120 may continue to collect data samples. If 804 is true, control may continue with 808.

At 808, the mobile computing device 108 may display a request to re-connect the disconnected sensor(s) on the touch display 212. At 812, the mobile computing device 108 may display a request to capture a second picture on the touch display 212. As described above, a first picture of the patient 112 may be captured before collection of the data samples begins.

Capturing another picture of the patient 112 after a disconnection of one or more of the sensors 124-139 may ensure that the data samples collected during the sleep study are for the patient 112. For example, the first picture taken before data collection began may be compared with the second picture taken after disconnection of one or more of the sensors 124-139. The comparison may be performed, for example, by the mobile computing device 108 using a facial recognition application or by a reviewer of data samples obtained during the sleep study after transmission to the sleep study server 116.

Figure 10B:
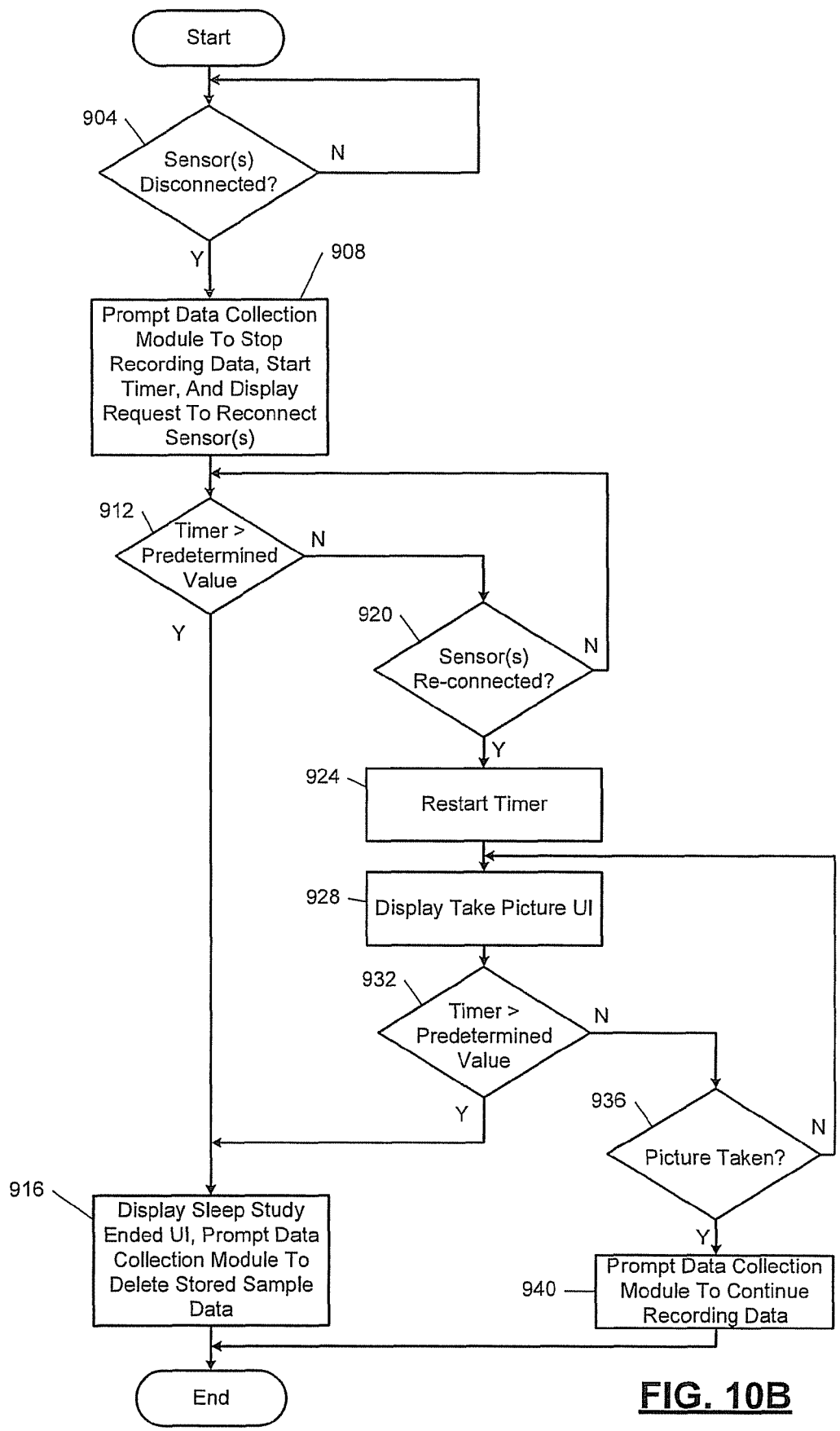

FIG. 10B is another flowchart depicting an example method of collecting data during a sleep study that may be performed by the mobile computing device 108 executing the sleep study application is presented. Referring now to FIG. 10B, control may begin while the data collection module 120 is collecting data samples for the sleep study.

At 904, the mobile computing device 108 may determine whether one or more of the sensors 124-139 have been disconnected. For example, the mobile computing device 108 may determine whether the SPO2 sensor 136 has been disconnected at 904. The mobile computing device 108 may additionally or alternatively determine whether the EOG sensor 137, the EMG sensor 124, and the ECG sensor 132 have been disconnected at 904. The mobile computing device 108 may additionally or alternatively determine whether the pressure sensor 138 and the temperature sensor 139 have been disconnected at 904. If 904 is true, control may continue with 908. If 904 is false, control may remain at 908. In various implementations, the sleep study may be allowed to continue despite disconnection of one or more sensors, such as disconnection of the EEG sensor 128. In various implementations, the mobile computing device 108 may require disconnection of the sensor(s) for at least a predetermined period before continuing with 908.

At 908, the mobile computing device 108 may prompt the data collection module 120 to stop storing data samples. The mobile computing device 108 may also start a timer and display a request to reconnect the disconnected sensor(s) on the touch display 212 at 908. In various implementations, the mobile computing device 108 may also generate one or more tactile alarms at 108, such as an audible alarm and/or a vibratory alarm.

The mobile computing device 108 may determine whether the timer is greater than a predetermined period (e.g., approximately 2 minutes or another suitable period) at 912. If 912 is true, control may continue with 916. If 912 is false, control may continue with 920. At 916, the mobile computing device 108 may display UI indicating that the sleep study has ended on the touch display 212 and prompt the data collection module 120 to delete stored data samples. Control may then end until a next execution of the sleep study application.

At 920, the mobile computing device 108 may determine whether the disconnected sensor(s) have been reconnected properly. If 920 is true, control may continue with 924. If 920 is false, control may continue to display the request to reconnect the disconnected sensor(s) and return to 912.

The mobile computing device 108 may reset and start the timer at 924. At 928, the mobile computing device 108 may display a request to capture a second image of patient 112 on the touch display 212. At 932, the mobile computing device 108 may determine whether the timer is greater than a predetermined period. If true, control may continue with 916, which is discussed above. If false, control may continue with 936.

At 936, the mobile computing device 108 may determine whether a second image of the patient 112 has been captured. If 936 is true, the mobile computing device 108 may prompt the data collection module 120 to continue storing data samples at 940, and control may continue with the sleep study. If 936 is false, control may return to 928 and continue displaying the request to capture a second picture of the patient 112.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. As used herein, the phrase at least one of A, B, and C should be construed to mean a logical (A or B or C), using a non-exclusive logical OR. It should be understood that one or more steps within a method may be executed in different order (or concurrently) without altering the principles of the present disclosure.

In this application, including the definitions below, the term module may be replaced with the term circuit. The term module may refer to, be part of, or include an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor (shared, dedicated, or group) that executes code; memory (shared, dedicated, or group) that stores code executed by a processor; other suitable hardware components that provide the described functionality; or a combination of some or all of the above, such as in a system-on-chip.

The term code, as used herein, may include software, firmware, and/or microcode, and may refer to programs, routines, functions, classes, and/or objects. The term shared processor encompasses a single processor that executes some or all code from multiple modules. The term group processor encompasses a processor that, in combination with additional processors, executes some or all code from one or more modules. The term shared memory encompasses a single memory that stores some or all code from multiple modules. The term group memory encompasses a memory that, in combination with additional memories, stores some or all code from one or more modules. The term memory may be a subset of the term computer-readable medium. The term computer-readable medium does not encompass transitory electrical and electromagnetic signals propagating through a medium, and may therefore be considered tangible and non-transitory. Non-limiting examples of a non-transitory tangible computer readable medium include nonvolatile memory, volatile memory, magnetic storage, and optical storage.

The apparatuses and methods described in this application may be partially or fully implemented by one or more computer programs executed by one or more processors. The computer programs include processor-executable instructions that are stored on at least one non-transitory tangible computer readable medium. The computer programs may also include and/or rely on stored data.

What is claimed is:

1. A mobile computing device for performing a sleep study, the mobile computing device comprising:
   a camera;
   a display;
   a processor;
   a tangible computer readable medium including a sleep study application embodied as code for:
      selectively displaying a request to capture an image of a user of the mobile computing device using the camera;
      storing the image;
      in response to the storage of the image, selectively triggering a data collection module to begin storing data samples generated based on signals generated using at least one of an electromyography (EMG) sensor connected to the user, an electroencephalography (EEG) sensor connected to the user, an electrocardiogram (ECG) sensor connected to the user, and an oxygen saturation (SPO2) sensor connected to the user, an electrooculography (EOG) sensor connected to the user, a temperature sensor connected to the user, and a pressure sensor connected to the user;
      in response to disconnection of at least one of the EMG sensor, the EEG sensor, the ECG sensor, the SPO2 sensor, the EOG sensor, the temperature sensor, and the pressure sensor, triggering the data collection module to stop storing data samples generated based on the signals;
      in response to a determination that the at least one of the EMG sensor, the EEG sensor, the ECG sensor, the SPO2 sensor, the EOG sensor, the temperature sensor, and the pressure sensor has/have been re-connected, displaying a second request to capture a second image of the user;
      storing the second image;
      in response to the storage of the second image, selectively triggering the data collection module to continue storing data samples generated based on the signals; and
      receiving the data samples from the data collection module.

2. The mobile computing device of claim 1 wherein the sleep study application further includes code for:
   displaying the request to capture an image of the user in response to a determination that the at least one of the EMG sensor, the EEG sensor, the ECG sensor, the SPO2 sensor, the EOG sensor, the temperature sensor, and the pressure sensor is/are properly connected to the user.

3. The mobile computing device of claim 1 wherein the sleep study application further includes code for:
   triggering the data collection module to stop storing data samples generated based on the signals in response to disconnection of the EMG sensor, the ECG sensor, and the EOG sensor.

4. The mobile computing device of claim 1 wherein the sleep study application further includes code for:
   triggering the data collection module to stop storing data samples generated based on the signals in response to disconnection of the SPO2 sensor.

5. The mobile computing device of claim 1 wherein the sleep study application further includes code for:
   transmitting sleep study data including the data samples, the image, and the second image to a data server.

6. The mobile computing device of claim 1 wherein the sleep study application further includes code for:
   displaying video obtained using the camera while displaying the request to capture an image of the user.

7. A method for performing a sleep study, comprising:
   selectively displaying on a display, by a mobile computing device, a request to capture an image of a user of the mobile computing device using a camera of the mobile computing device;
   storing, by the mobile computing device, the image in a tangible computer readable medium; and
   in response to the storage of the image:
      selectively triggering, by the mobile computing device, a data collection module to begin storing data samples generated based on signals generated using at least one of an electromyography (EMG) sensor connected to the user, an electroencephalography (EEG) sensor connected to the user, an electrocardiogram (ECG) sensor connected to the user, and an oxygen saturation (SPO2) sensor connected to the user, an electrooculography (EOG) sensor connected to the user, a temperature sensor connected to the user, and a pressure sensor connected to the user;
   by the mobile computing device, triggering the data collection module to stop storing data samples generated based on the signals in response to disconnection of at least one of the EMG sensor, the EEG sensor, the ECG sensor, the SPO2 sensor, the EOG sensor, the temperature sensor, and the pressure sensor;
   displaying, by the mobile computing device, a second request to capture a second image of the user in response to a determination that the at least one of the EMG sensor, the EEG sensor, the ECG sensor, the SPO2 sensor, the EOG sensor, the temperature sensor, and the pressure sensor has/have been re-connected;
   storing, by the mobile computing device, the second image in the tangible computer readable medium;
   by the mobile computing device, triggering the data collection module to continue storing data samples generated based on the signals in response to the storage of the second image; and
   receiving, by the mobile computing device, the data samples from the data collection module.

8. The method of claim 7 further comprising:
   displaying, by the mobile computing device, the request to capture an image of the user in response to a determination that the at least one of the EMG sensor, the EEG sensor, the ECG sensor, the SPO2 sensor, the EOG sensor, the temperature sensor, and the pressure sensor is/are properly connected to the user.

9. The method of claim 7 further comprising:
triggering, by the mobile computing device, the data collection module to stop storing data samples generated based on the signals in response to disconnection of the EMG sensor, the ECG sensor, and the EOG sensor.

10. The method of claim 7 further comprising:
triggering, by the mobile computing device, the data collection module to stop storing data samples generated based on the signals in response to disconnection of the SPO2 sensor.

11. The method of claim 7 further comprising:
transmitting, by the mobile computing device, sleep study data including the data samples, the image, and the second image to a data server.

12. The method of claim 7 further comprising:
displaying on the display, by the mobile computing device, video obtained using the camera while displaying the request to capture an image of the user.

13. The method of claim 7 further comprising:
comparing, by the mobile computing device, the image of the user with the second image of the user.

14. The mobile computing device of claim 1 wherein the sleep study application further includes code for comparing the image of the user with the second image of the user.

* * * * *